US011935381B2

(12) United States Patent
Shiina

(10) Patent No.: US 11,935,381 B2
(45) Date of Patent: Mar. 19, 2024

(54) FIRE DETECTION SYSTEM AND FIRE DETECTION METHOD

(71) Applicant: NEC Corporation, Tokyo (JP)

(72) Inventor: Misao Shiina, Tokyo (JP)

(73) Assignee: NEC CORPORATION, Tokyo (JP)

( * ) Notice: Subject to any disclaimer, the term of this patent is extended or adjusted under 35 U.S.C. 154(b) by 563 days.

(21) Appl. No.: 17/259,369

(22) PCT Filed: Apr. 10, 2019

(86) PCT No.: PCT/JP2019/015588
§ 371 (c)(1),
(2) Date: Jan. 11, 2021

(87) PCT Pub. No.: WO2020/021780
PCT Pub. Date: Jan. 30, 2020

(65) Prior Publication Data
US 2021/0304578 A1    Sep. 30, 2021

(30) Foreign Application Priority Data

Jul. 23, 2018  (JP) .................................. 2018-137798

(51) Int. Cl.
*G08B 17/117* (2006.01)
*G01H 9/00* (2006.01)
(Continued)

(52) U.S. Cl.
CPC ........... *G08B 17/117* (2013.01); *G01H 9/004* (2013.01); *G01K 3/005* (2013.01); *G01K 11/32* (2013.01);
(Continued)

(58) Field of Classification Search
CPC ........................ B60C 23/0488; B60C 23/0462
See application file for complete search history.

(56) References Cited

U.S. PATENT DOCUMENTS

2018/0073982 A1*   3/2018  Ebata ..................... G01N 21/61

FOREIGN PATENT DOCUMENTS

| CN | 101393444 A |   | 3/2009 |
| CN | 104635639 A | * | 5/2015 |

(Continued)

OTHER PUBLICATIONS

International Search Report for PCT Application No. PCT/JP2019/015588, dated Jun. 25, 2019.

(Continued)

*Primary Examiner* — Daniell L Negron

(57) ABSTRACT

The fire detection system is provided to enable early detection of a location where a fire may occur. When detecting a location which vibration reached in the optical fiber 104, the sensor unit 102 transmits information indicating the location to the information output unit 101. The gas state detection section 103 transmits information indicating the state of gas to the information output unit 101. The information output unit 101 receives the information indicating the location which the vibration reached in the optical fiber 104 and the information indicating the state of gas, and outputs information indicating a sign of a fire outbreak occurred when the state of gas meets a predetermined condition.

5 Claims, 20 Drawing Sheets

(51) Int. Cl.
  *G01K 3/00*       (2006.01)
  *G01K 11/32*      (2021.01)
  *G01N 21/31*      (2006.01)
  *G01N 33/00*      (2006.01)

(52) U.S. Cl.
  CPC .......... *G01N 21/31* (2013.01); *G01N 33/004* (2013.01); *G01N 2201/06113* (2013.01)

(56) References Cited

FOREIGN PATENT DOCUMENTS

| JP | S58-078290 A   | 5/1983 |
| JP | S59-166803 A   | 9/1984 |
| JP | H04-48398 A    | 2/1992 |
| JP | H11-120457 A   | 4/1999 |
| JP | 2005-083876 A  | 3/2005 |
| JP | 2012-088752 A  | 5/2012 |
| JP | 2017-134681 A  | 8/2017 |

OTHER PUBLICATIONS

Y. Chen, et al., "Development of a Fire Detection System Using FT-IR Spectroscopy and Artificial Neural Networks", Fire Safety Science Proceedings of the 6th International Symposium, 2000, pp. 791-802, USA.

Japanese Office Action for JP Application No. 2020-532156 dated Feb. 1, 2022 with English Translation.

\* cited by examiner

FIRE DETECTION SYSTEM AND FIRE DETECTION METHOD

This application is a National Stage Entry of PCT/JP2019/015588 filed on Apr. 10, 2019, which claims priority from Japanese Patent Application 2018-137798 filed on Jul. 23, 2018 the contents of all of which are incorporated herein by reference, in their entirety.

TECHNICAL FIELD

The present invention relates to a fire detection system and a fire detection method, and an information output device applied to the fire detection system.

BACKGROUND ART

Various types of disaster prevention systems have been proposed (refer to patent literatures 1-3, for example).

The patent literature 1 describes a tunnel disaster prevention system including a fiber-optic temperature measurement system in which temperature measurement points are determined at equal intervals. Furthermore, the tunnel disaster prevention system described in the patent literature 1 including a carbon monoxide (hereinafter referred to as "CO") concentration measurement system in which a CO sensor is installed at each measurement point of CO.

The patent literature 2 describes a disaster prevention system having a laser irradiation means and a laser light-receiving means, and calculating the concentration of a specific gas in a subway premises using a laser absorption method.

The patent literature 3 describes a fire and intrusion detection system using an optical fiber. The patent literature 3 describes detecting heat applied to an optical fiber as well as detecting a location where heat is applied in the optical fiber. It is also described in the patent literature 3 that a strain or vibration of an optical fiber is detected, and a location where the strain or vibration has occurred in the optical fiber is identified.

CITATION LIST

Patent Literatures

PTL 1: Japanese Patent Application Laid-Open No. Hei11-120457
PTL 2: Japanese Patent Application Laid-Open No. 2005-83876
PTL 3: Japanese Patent Application Laid-Open No. 2017-134681

SUMMARY OF INVENTION

Technical Problem

It is considered to detect a fire outbreak in a tunnel, for example, by identifying the location of a temperature rise using optical fibers.

However, it takes a long time for the ambient temperature of the optical fiber to rise above a predetermined value after a fire has broken out. Therefore, it takes a long time to detect a fire outbreak.

Therefore, it is an object of the present invention to provide a fire detection system and a fire detection method capable of early detection of locations where there is a possibility of fire outbreak, and an information output device applied to the fire detection system.

It is also an object of the present invention to provide a fire detection system and a fire detection method capable of early detection of a section where a fire may beak out prior to detection of a fire outbreak location, and an information output device applied to the fire detection system.

Solution to Problem

A fire detection system according to the present invention includes: one or more sensor units installed in an optical fiber, a gas state detection unit which detects a state of gas, and an information output unit which outputs information, wherein when detecting a location which vibration reached in the optical fiber, the sensor unit transmits information indicating the location to the information output unit, the gas state detection unit transmits information indicating the state of gas to the information output unit, and the information output unit receives the information indicating the location which the vibration reached in the optical fiber and the information indicating the state of gas, and outputs information indicating a sign of a fire outbreak occurred when the state of gas meets a predetermined condition.

A fire detection system according to the present invention includes: one or more sensor units installed in an optical fiber, a gas state detection unit which detects a state of gas, and an information output unit which outputs information, wherein the gas state detection unit transmits information indicating the state of gas to the information output unit, when detecting a location where a temperature rise has occurred in the optical fiber, the sensor unit transmits information indicating the location to the information output unit, and the information output unit receives the information indicating the state of gas, outputs information indicating a sign of a fire outbreak occurred when the state of gas meets a predetermined condition, and outputs information indicating a fire has occurred at the location when receiving the information indicating the location.

An information output device according to the present invention is configured to: receive information indicating a location which vibration reached in an optical fiber from a sensor unit installed in the optical fiber, receive information indicating a state of gas from a gas state detection unit which detects the state of gas, and output information indicating a sign of a fire outbreak occurred at the location when the state of gas meets a predetermined condition.

An information output device according to the present invention is configured to: receive information indicating a state of gas from a gas state detection unit which detects the state of gas, output information indicating a sign of a fire outbreak occurred at the location when the state of gas meets a predetermined condition, and when receiving information indicating a location where a temperature rise occurred in an optical fiber from a sensor unit installed in the optical fiber, output information indicating that a fire has broken out at the location.

A fire detection method according to the present invention is applied to a fire detection system including a sensor unit installed in an optical fiber, a gas state detection unit for detecting a state of gas, and an information output unit for outputting information, wherein information indicating the location is transmitted to the information output unit, by the sensor unit, when a location which vibration reached in the optical fiber is detected, information indicating the state of gas is transmitted to the information output unit, by the gas state detection unit, and information indicating a sign of a fire outbreak occurred is output by the information output unit, when the information indicating the location which the vibration reached in the optical fiber is received, the information indicating the state of gas is received, and the state of gas meets a predetermined condition.

A fire detection method according to the present invention is applied to a fire detection system including a sensor unit installed in an optical fiber, a gas state detection unit for detecting a state of gas, and an information output unit for outputting information, wherein information indicating the state of gas is transmitted to the information output unit, by the gas state detection unit, when a location where a temperature rise has occurred in the optical fiber is detected, information indicating the location is transmitted to the information output unit, by the sensor unit, information indicating a sign of a fire outbreak occurred is output by the information output unit, when the information indicating the state of gas is received and the state of gas meets a predetermined condition, and information indicating a fire has occurred at the location is output by the information output unit, when the information indicating the location is received.

Advantageous Effects of Invention

According to the present invention, it is possible to detect locations early where there is a possibility of fire outbreak.

According to the present invention, it is possible to detect a section early where there is a possibility of fire before the detection of a fire outbreak location.

DESCRIPTION OF EMBODIMENT

Hereinafter, exemplary embodiments of the present invention will be described with reference to appended drawings.

Exemplary Embodiment 1

Figure 1:
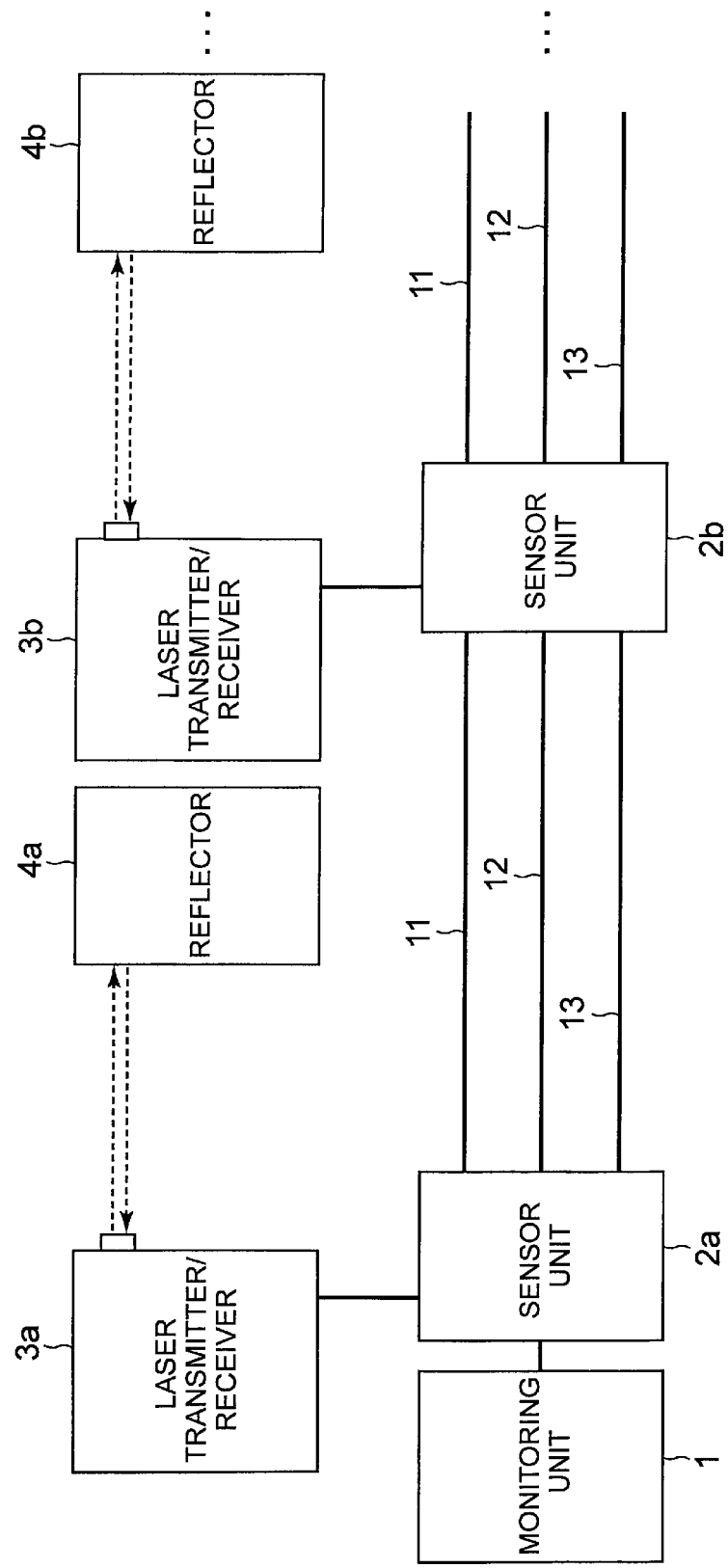
FIG. 1 It depicts a block diagram showing an example of a fire detection system in a first exemplary embodiment of the present invention.

FIG. 1 is a block diagram illustrating an example of a fire detection system of a first exemplary embodiment of the present invention. The fire detection system of the first exemplary embodiment comprises a monitoring unit 1, a plurality of sensor units 2, and a plurality of pairs of a laser transmitter/receiver 3 and a reflector 4.

Each of sensor units 2 is provided so that a first optical fiber 11, a second optical fiber 12 and a third optical fiber 13 pass through.

The first optical fiber 11, the second optical fiber 12, the third optical fiber 13, each sensor unit 2, each pair of the laser transmitter/receiver 3 and the reflector 4, are located, for example, in the tunnel. The monitoring unit 1 is located, for example, in an operation room where an operator is present.

The laser transmitter/receivers are represented by the sign "3", however, when each laser transmitter/receiver is identified, the sign "3" is followed by a subscript such as "a". In the same way, the reflectors are represented by the sign "4", however, when each reflector is identified, the sign "4" is followed by a subscript such as "a". Similarly, the sensor units are represented by the sign "2", however, when each sensor unit is identified, the sign "2" is followed by a subscript such as "a". That manner is the same in the second exemplary embodiment described below.

The laser transmitter/receiver 3 and the reflector 4 are paired. The distance between the laser transmitter/receiver 3 and the reflector 4 is about 300 m, but is not limited to about 300 m.

In the example shown in FIG. 1, one sensor unit 2 and one pair of a laser transmitter/receiver 3 and a reflector 4 are mapped one-to-one. For example, in the example shown in FIG. 1, one sensor unit 2a is mapped to a pair of a laser transmitter/receiver 3a and a reflector 4a.

Figure 2:
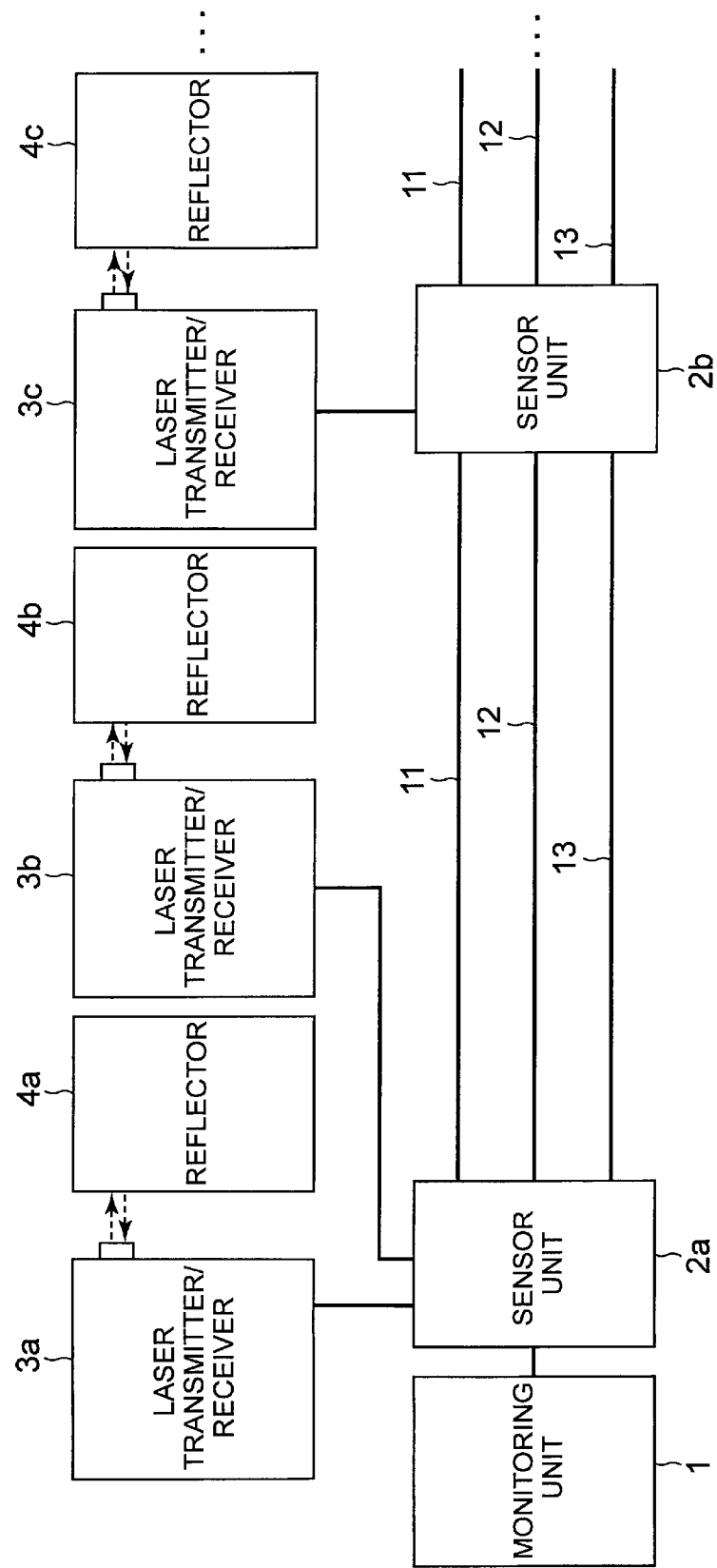
FIG. 2 It depicts a schematic diagram showing an example in which a plurality of pairs of a laser transmitter/receiver and a reflector are associated with a single sensor unit.

However, the distance between the sensor units 2 can be longer than the distance between the laser transmitter/receiver 3 and the reflector 4 (e.g., about 300 m). Therefore, as shown in FIG. 2, a plurality of pairs of the laser transmitter/receivers 3 and the reflectors 4 may be provided between a sensor units 2 and the other sensor unit 2, and a plurality of pairs of the laser transmitter/receivers 3 and the reflectors 4 may be associated with one sensor unit 2. For example, in the example shown in FIG. 2, a pair of a laser transmitter/receiver 3a and a reflector 4a, and a pair of a laser transmitter/receiver 3b and a reflector 4b are associated with the sensor unit 2a.

To simplify the explanation, the following is an example of a one-to-one correspondence between one sensor unit 2 and one pair of a laser transmitter/receiver 3 and a reflector 4, as shown in FIG. 1.

The laser transmitter/receiver 3 is communicably connected to the corresponding sensor unit 2. The laser transmitter/receiver 3 and the sensor unit 2 may be connected wirelessly, but it is more preferable to be connected by a wire.

As mentioned above, each of sensor units 2 is provided so that a first optical fiber 11, a second optical fiber 12 and a third optical fiber 13 pass through. In the example shown in FIG. 1, it is assumed that the sensor unit 2a, which is communicably connected to the monitoring unit 1, is the most upstream sensor, and the other sensor units 2 (such as the sensor unit 2b) are sequentially located downstream. However, as described below, the plurality of sensor units 2 may be connected in a looped manner.

The first optical fiber 11 is used to detect the occurrence of the accident-based vibration and the location of the occurrence of the vibration. In other words, the first optical fiber 11 is used to detect that the accident-based vibration transmitted to the first optical fiber 11 and the location which the vibration reached in the first optical fiber 11.

The second optical fiber 12 is used to detect the temperature rise based on fire outbreak and a location where the temperature rise has occurred.

The third optical fiber 13 is used to notify the monitoring unit 1 of a location which vibration reached in the first optical fiber 11 and a location where a temperature rise has occurred in the second optical fiber 12. The third optical fiber 13 is also used to transmit the information derived by the laser transmitter/receiver 3a to the monitoring unit 1. The use of the third optical fiber 13 is not limited to the above examples and may be used to transmit other information (e.g., a log, etc.) to the monitoring unit 1.

Each sensor unit 2 uses the first optical fiber 11 and the second optical fiber 12 to output light downstream. The first optical fiber 11 and the second optical fiber 12 transmit light downstream. However, even if the sensor unit 2 outputs light downstream, the back-scattered light (optical feedback) in the first optical fiber 11 and the second optical fiber 12 may return to the sensor unit 2.

Each sensor unit 2 emits light to the first optical fiber 11, and when the sensor unit 2 detects a location which the vibration reached in the first optical fiber 11 between the sensor unit 2 and the next sensor unit 2 downstream of the sensor unit 2, the information indicating the location is transmitted to the sensor unit 2a at the most upstream side, using the third optical fiber 13. The sensor unit 2a transmits the information indicating the location to the monitoring unit 1.

Each sensor unit 2 emits light to the second optical fiber 12, and when the individual sensor unit 2 detects a location between the sensor unit 2 and the next sensor unit 2 downstream of the sensor unit 2 where a temperature rise has occurred in the second optical fiber 12, the information indicating the location is transmitted to the sensor unit 2a at the most upstream side, using the third optical fiber 13. The sensor unit 2a transmits the information indicating the location to the monitoring unit 1. Here, the temperature rise shall mean that the temperature rises above a predetermined value.

Each laser transmitter/receiver 3 is assigned a monitored section for a state of gas. The section between the laser transmitter/receiver 3 and the reflector 4, which is paired with the laser transmitter/receiver 3, is the monitored section assigned to that laser transmitter/receiver 3. For example, the section between the laser transmitter/receiver 3a and the reflector 4a is the monitored section assigned to the laser transmitter/receiver 3a.

Each laser transmitter/receiver 3 detects the state of gas in the assigned monitored section. The laser transmitter/receiver 3 detects, for example, the concentration of a single or multiple gases. In this exemplary embodiment and a second exemplary embodiment described below, each laser transmitter/receiver 3 detects the concentration of carbon monoxide (CO) and the concentration of carbon dioxide (hereinafter referred to as $CO_2$) in the monitored section. The ratio of the concentration of CO to the concentration of $CO_2$ in the monitored section is derived by detecting the concentration of CO and the concentration of $CO_2$ in the monitored section. That is, when the concentration of CO detected in the monitored section is set to x [ppm] and the concentration of $CO_2$ detected in the monitored section is set to y [ppm], the laser transmitter/receiver 3 derives "x/y", which is the ratio of x to y.

When the ratio "x/y" of the concentration of CO to the concentration of $CO_2$ in the monitored section is greater than a predetermined threshold (described as T) that is predetermined, the laser transmitter/receiver 3 transmits information indicating that the ratio "x/y" is greater than the threshold T, and information indicating the monitored section assigned to the laser transmitter/receiver 3 to the monitoring unit 1 via the sensor unit 2 connected to the laser transmitter/receiver 3. When the sensor unit 2 connected to the laser transmitter/receiver 3 receives from the laser transmitter/receiver 3 the information indicating that "x/y" is greater than the threshold T and the information indicating the monitored section assigned to the laser transmitter/receiver 3, the sensor unit 2 transmits the information to the sensor unit 2a at the most upstream side. The sensor unit 2a transmits the information to the monitoring unit 1. The information indicating the monitored section may be, for example, the ID of the monitored section, or it may be, for example, the ID of the laser transmitter/receiver 3 corresponding to the monitored section.

When the ratio of CO concentration to $CO_2$ concentration, x/y, is greater than the threshold T, it means that a sign of a fire outbreak has occurred within the monitored section. However, the event which means that a sign of a fire outbreak has occurred within the monitored section is not limited to the event that the ratio "x/y" is greater than the threshold T. Other events that indicate that a sign of a fire outbreak has occurred within the monitored section are described below.

Figure 3:
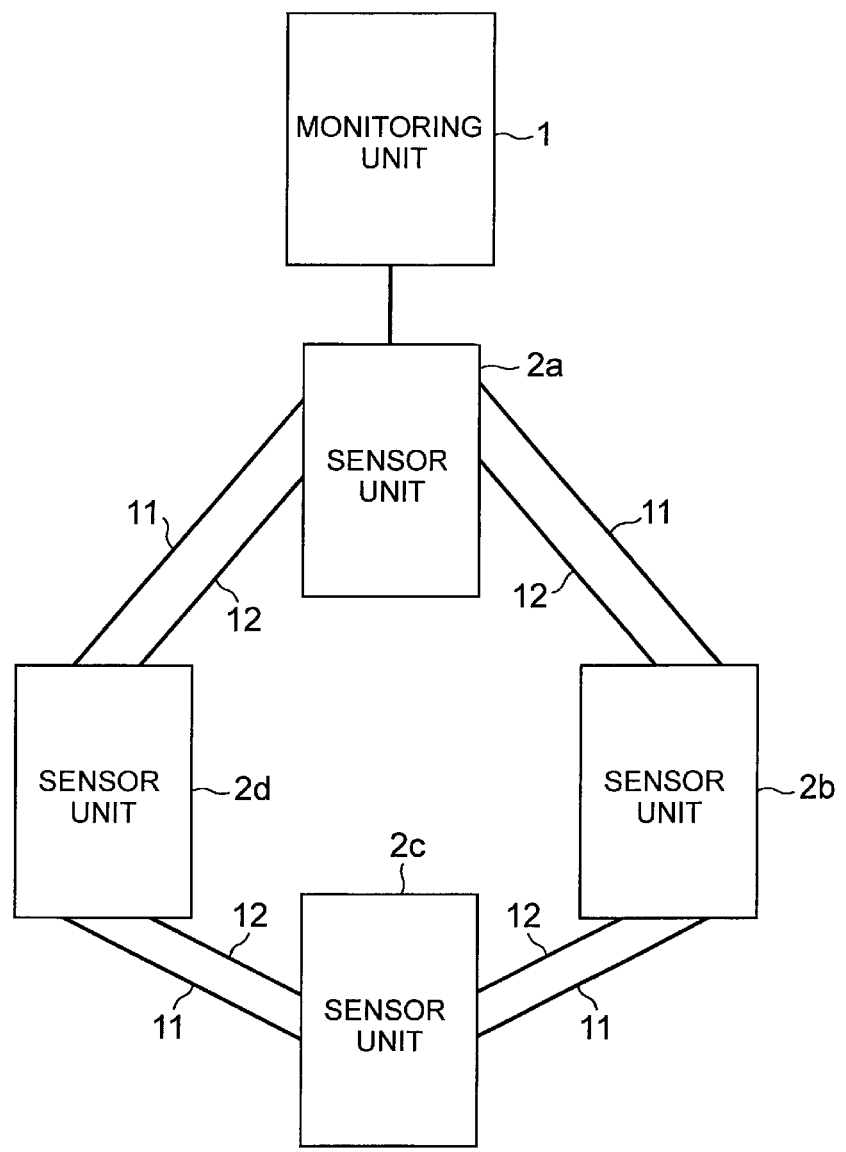
FIG. 3 It depicts a schematic diagram showing an example in which the sensor units are installed in a loop shape.

The sensor units 2 may be installed in a loop shape. FIG. 3 is a schematic diagram illustrating an example in which the sensor units 2 are installed in a loop shape. In FIG. 3, the pair of a laser transmitter/receiver 3 and a reflector 4 corresponding to each sensor unit 2 is omitted. Although FIG. 3 shows four sensor units 2a-4d, the number of sensor units 2 is not limited to four. When the sensor units 2 are installed in a looped manner, a third optical fiber 13 need not be provided. When the sensor unit 2 receives information indicating that "x/y" is greater than the threshold T and information indicating the monitored section from the laser transmitter/receiver 3, the sensor unit 2 may transmit the information using either the first optical fiber 11 or the second optical fiber 12 to the sensor unit 2a connected to the monitoring unit 1. The sensor unit 2a may transmit the information to the monitoring unit 1. In addition, when either sensor unit 2 transmits to the monitoring unit 1 information indicating a location which vibration reached in the first optical fiber 11, or transmits to the monitoring unit 1 information indicating a location where a temperature rise has occurred in the second optical fiber 12, either the first optical fiber 11 or the second optical fiber 12 can be used. Although the first optical fiber 11 and the second optical fiber 12 allow light to pass through in one direction, since each sensor unit 2 is installed in a loop, any sensor unit 2 can transmit information to the monitoring unit 1 through the sensor unit 2a. However, in each exemplary embodiment, for the sake of simplicity of explanation, each exemplary embodiment will be described using the case where one sensor unit 2a is connected to the monitoring unit 1, as shown in FIG. 1, with the sensor unit 2a as the most upstream sensor and the other sensor units 2 sequentially disposed downstream, as an example.

Figure 4:
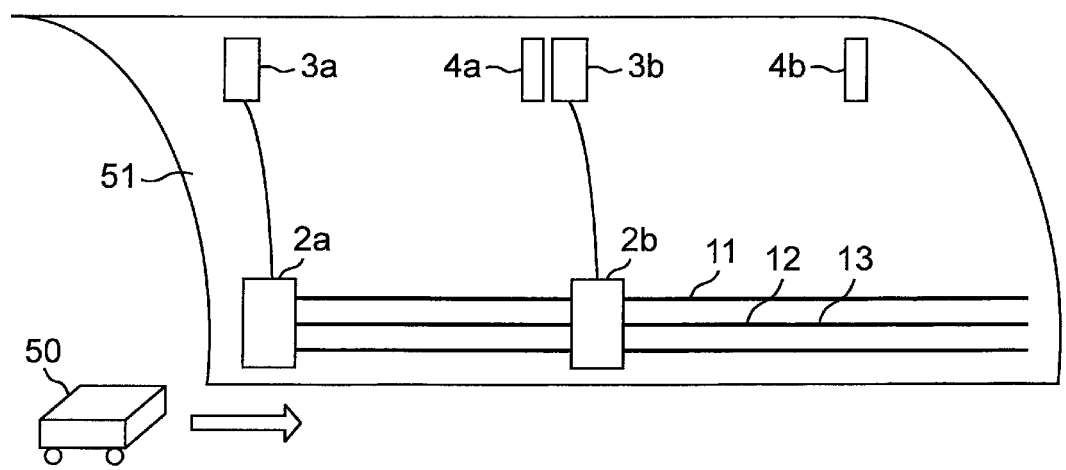
FIG. 4 It depicts a schematic diagram showing an example of the arrangement of a sensor unit, a laser transmitter/receiver and a reflector in a tunnel.

FIG. 4 is a schematic diagram showing an example arrangement of the sensor unit 2, the laser transmitter/receiver 3 and the reflector 4 in a tunnel. Elements identical to those shown in FIG. 1 are marked with the same sign as in FIG. 1. In FIG. 4, the monitoring unit 1 is omitted. FIG. 4 schematically illustrates a situation of the tunnel as seen from the inside, and to make it easier to understand that the tunnel is viewed from the inside, a vehicle 50 traveling through the tunnel is also illustrated in FIG. 4.

The laser transmitter/receiver 3 and the reflector 4 are installed, for example, at a high position on the wall 51 inside the tunnel (refer to FIG. 4). The first optical fiber 11, the second optical fiber 12, and the third optical fiber 13, as well as the respective sensor unit 2, are installed, for example, at a lower position on the wall 51 inside the tunnel (refer to FIG. 4). However, each sensor unit 2 may be installed at a higher position of the wall 51 while the first optical fiber 11, the second optical fiber 12 and the third optical fiber 13 may be installed at a lower position of the wall 51 and these optical fibers are pulled around.

The monitoring unit 1 is, for example, communicably connected to one sensor unit 2. The monitoring unit 1 may be communicably connected to a plurality of sensor units 2. In each exemplary embodiment, to simplify the explanation, the monitoring unit 1 is connected to one sensor unit 2a as an example. As mentioned above, the monitoring unit 1 is located in an operation room where an operator is present. The monitoring unit 1 is implemented by an information processing device such as a computer, for example, and includes a display. The monitoring unit 1 may also include an audio output device (e.g., a speaker), an input device (e.g., a keyboard) for an operator to enter commands, and the like. The monitoring unit 1 may be referred to as an information output device.

The monitoring unit 1 receives information transmitted by the laser transmitter/receiver 3 and the sensor unit 2, and outputs various information based on the received information. In each exemplary embodiment, the monitoring unit 1 outputs the information by displaying the information on a display (not shown in the figure) as an example. However, the method of outputting the information of the monitoring unit 1 is not limited to displaying the information. The method may output the information as audio for example.

In general, a fires in a tunnel, etc., occurs in the following course of events. First, there is an accident of a vehicle. A vibration occurs on the basis of the accident. Later, a state of gas at the accident location will indicate a sign of a fire outbreak. Further, a fire then breaks out at the location.

Accordingly, the monitoring unit 1 first receives information on the location which the vibration reached in the first optical fiber 11 from the sensor unit 2, which detects that the vibration based on the accident reached to the first optical fiber 11. At this time, the monitoring unit 1 displays the location on the display and also displays information that there is a possibility of occurring an accident at the location.

Next, the laser transmitter/receiver 3, to which the monitored section including the location is assigned, transmits to the monitoring unit 1, when the ratio "x/y" of the concentration of CO to the concentration of $CO_2$ is greater than the threshold T, information that the ratio "x/y" is greater than the threshold T, and information indicating the monitored section, and the monitoring unit 1 receives the information.

When the monitoring unit 1 receives information that the ratio of the concentration of CO to the concentration of $CO_2$, "x/y", is greater than the threshold T, and information indicating the monitored section, the monitoring unit 1 determines whether or not the location which the vibration reached in the first optical fiber 11 is within the monitored section. If the location is within the monitored section, the monitoring unit 1 determines that a sign of a fire outbreak has occurred at the location, and displays the information that a sign of a fire outbreak has occurred at the location on the display.

Here, the laser transmitter/receiver 3 can detect that the ratio of CO concentration to $CO_2$ concentration, "x/y", is greater than the threshold T within the monitored section. The laser transmitter/receiver 3 cannot specify the location where the ratio "x/y" is greater than the threshold T in the monitored section. However, the monitoring unit 1 first receives information about the location which the vibration reached in the first optical fiber 11, and then receives information that the ratio "x/y" is greater than the threshold T, and information indicating the monitored section. Accordingly, by the fact that the location is within the monitored section, the monitoring unit 1 identifies the location where a sign of a fire outbreak occurred as the same location which the vibration reached in the first optical fiber 11, and specifically displays the location where a sign of a fire outbreak occurred on the display.

As described above, the monitoring unit 1 determines that a sign of a fire outbreak has occurred at the location, when the location which the vibration reached in the first optical fiber 11 is within the notified monitored section and a state of gas meets a predetermined condition (x/y>T, in this example), and outputs information that a sign of a fire outbreak has occurred at the location.

Further, if a fire breaks out at the location where the accident occurred, the monitoring unit 1 receives information from the sensor unit 2, which detected the temperature rise in the second optical fiber 12, about the location where the temperature rise occurred in the second optical fiber 12.

When the monitoring unit 1 receives the information, the monitoring unit 1 displays on a display the information that a fire has broken out at the location where the temperature rise has occurred at the second optical fiber 12. This location can be said to be approximately the same location which the vibration reached in the first optical fiber 11.

Figure 5:
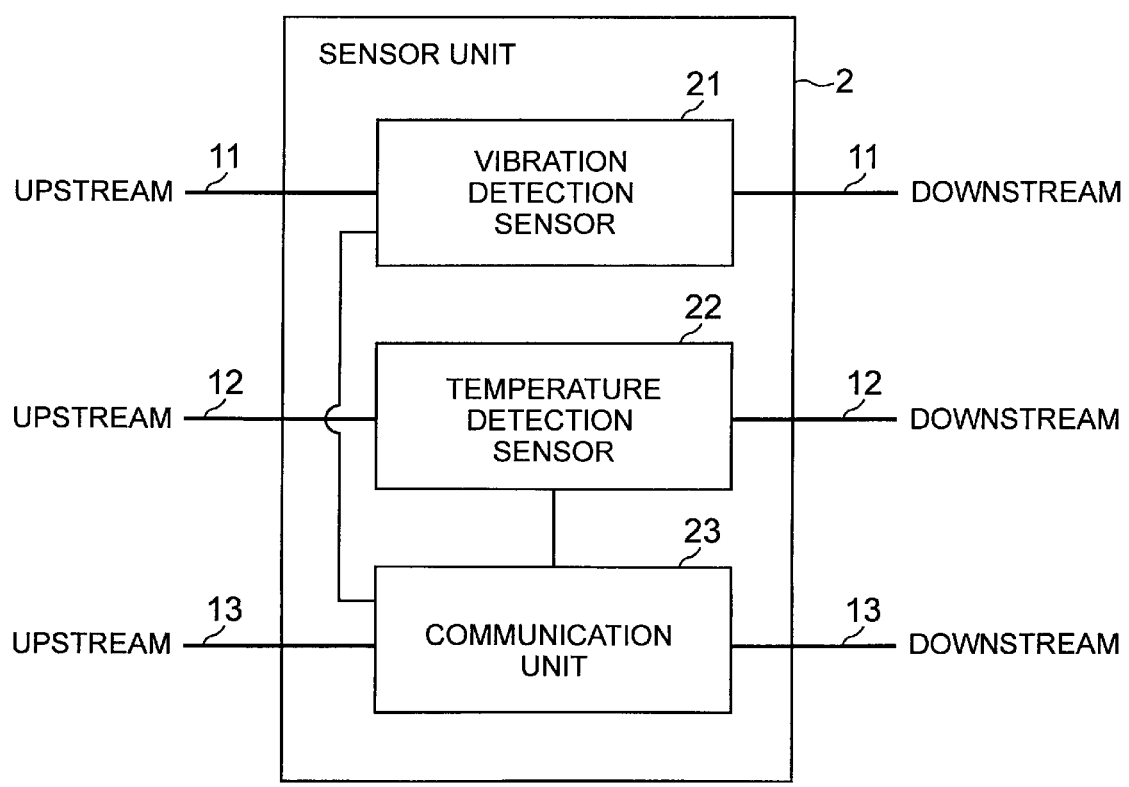
FIG. 5 It depicts a block diagram illustrating an example configuration of the sensor unit.

FIG. 5 is a block diagram illustrating an example configuration of the sensor unit 2. The sensor unit 2 includes a vibration detection sensor 21, a temperature detection sensor 22, and a communication unit 23.

The vibration detection sensor 21 transmits light to the downstream side using the first optical fiber 11. The vibration detection sensor 21 may emit the light received from the sensor unit 2 at the upstream side via the first optical fiber 11 to the downstream side. The vibration detection sensor 21 determines, for example, based on the backscattered light, whether or not vibration was transmitted to the first optical fiber 11 from the sensor unit 2 to the next sensor unit 2 downstream. When the vibration detection sensor 21 determines the vibration was transmitted to the first optical fiber 11, the vibration detection sensor 21 detects the location which the vibration reached in the first optical fiber 11.

The method of determining whether or not vibration was transmitted to the first optical fiber 11 and the method of detecting the location where vibration was transmitted in the first optical fiber 11 may be a known method, for example, the method described in Patent Literature 3.

When an accident occurs in a tunnel, vibration caused by the accident has been transmitted to the first optical fiber 11 in the vicinity of the accident location. The vibration detection sensor 21 then determines that the vibration was transmitted to the first optical fiber 11 between the sensor unit 2 and the next sensor unit 2 downstream, and furthermore detects a location which the vibration reached in the first optical fiber 11. The vibration detection sensor 21 then transmits information indicating the location which the vibration reached in the first optical fiber 11 to the communication unit 23.

Sound is also a type of vibration. The vibration detection sensor 21 may detect that vibration of a high frequency that is recognized as a sound by a human being was transmitted to the first optical fiber 11 and the location which the vibration reached in the first optical fiber 11. The sensor unit 2 may includes a sensor for detecting that vibration (here, vibration of a low frequency that is not recognized as a sound by a human being) was transmitted to the first optical fiber 11 and a location which the vibration reached in the first optical fiber 11, and an another sensor for detecting that sound was transmitted to the first optical fiber 11 and a location which the sound reached in the first optical fiber 11.

The temperature detection sensor 22 transmits light to the downstream side using the second optical fiber 12. The temperature detection sensor 22 may emit the light received from the sensor unit 2 at the upstream side via the second optical fiber 12 to the downstream side. The temperature detection sensor 22 determines, for example, based on the backscattered light, whether or not a temperature rise has occurred in the second optical fiber 12 from the sensor unit 2 to the next sensor unit 2 downstream. When the temperature detection sensor 22 determines that the temperature rise has occurred in the second optical fiber 12, the temperature detection sensor 22 detects a location where the temperature rise has occurred in the second optical fiber 12. As already explained, a temperature rise shall mean that the temperature rises above a predetermined value.

The method of determining whether or not a temperature rise has occurred in the second optical fiber 12 and the method of detecting a location where a temperature rise has occurred in the second optical fiber 12 may be a known method, for example, the method described in Patent Literature 3.

When a fire breaks out in a tunnel, the heat of the fire is transferred to the second optical fiber 12 in the vicinity of the fire outbreak location. Then, the temperature detection sensor 22 determines that a temperature rise has occurred in the second optical fiber 12 from the sensor unit 2 to the next sensor unit 2 downstream, and furthermore detects a location where the temperature rise has occurred in the second optical fiber 12. The temperature detection sensor 22 then transmits information indicating the location where the temperature rise has occurred at the second optical fiber 12 to the communication unit 23.

The communication unit 23 transmits the information obtained from the vibration detection sensor 21, which indicates the location which the vibration reached in the first optical fiber 11, to the monitoring unit 1. Similarly, the communication unit 23 transmits the information obtained from the temperature detection sensor 22, which indicates the location where the temperature rise occurred in the second optical fiber 12, to the monitoring unit 1.

Further the communication unit 23 receives from the laser transmitter/receiver 3 (not shown in FIG. 5), which is connected to the sensor unit 2, information that the ratio "x/y" of the concentration of CO to the concentration of $CO_2$ is greater than the threshold T and information indicating the monitored section, and transmits the information to the monitoring unit 1.

When the communication unit 23 transmits the various information described above to the monitoring unit 1, the communication unit 23 transmits the information to the sensor unit 2a at the most upstream side using the third optical fiber 13. The sensor unit 2a then transmits the information to the monitoring unit 1.

When the downstream sensor unit 2 transmits the above information to the monitoring unit 1, the communication unit 23 relays the information to the upstream sensor unit 2.

Figure 6:
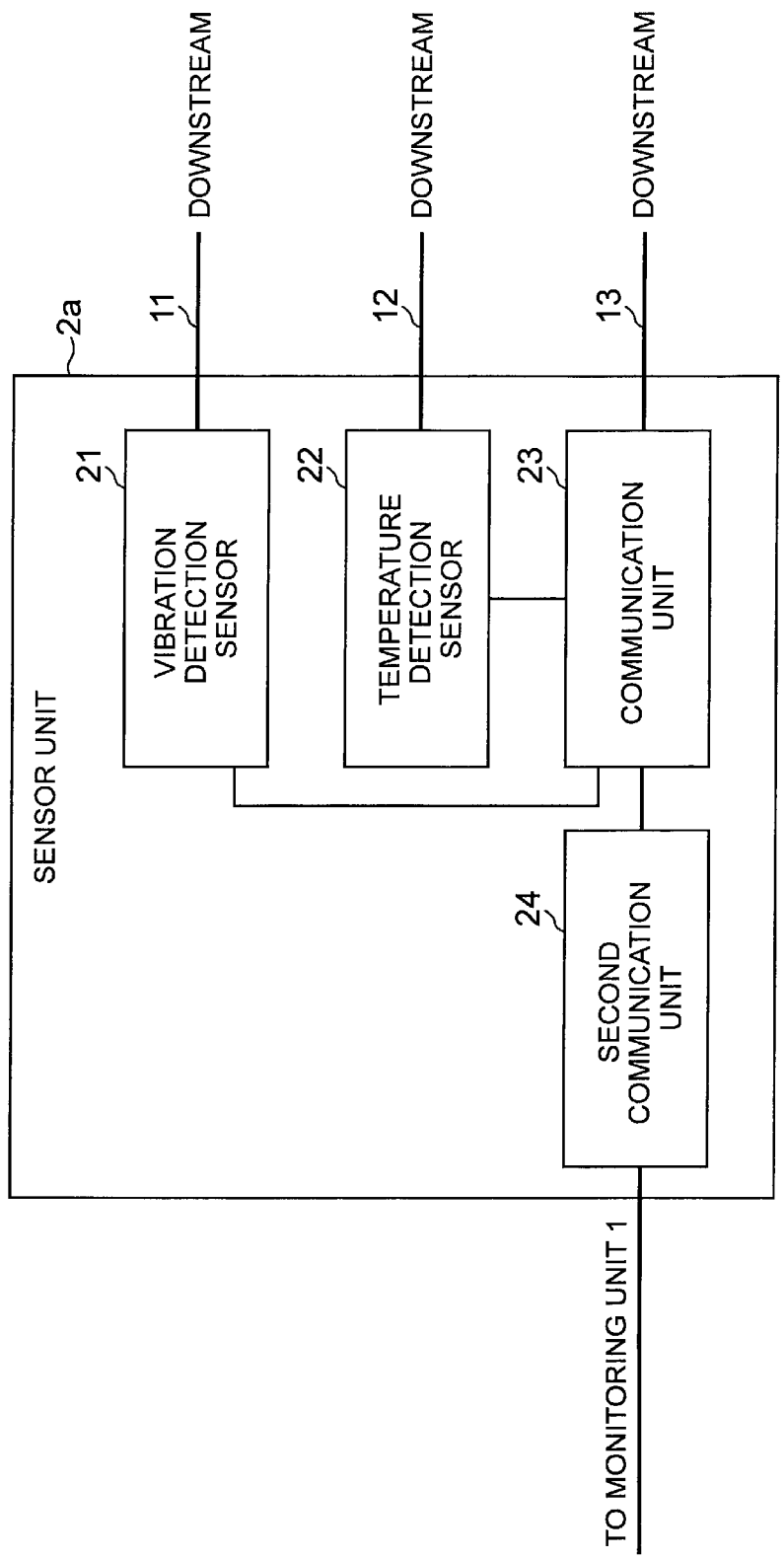
FIG. 6 It depicts a block diagram showing an example configuration of the sensor unit connected to the monitoring unit.

FIG. 6 is a block diagram showing an example configuration of the sensor unit 2a at the most upstream side (sensor unit 2a connected to the monitoring unit 1). Elements similar to those shown in FIG. 5 are marked with the same sign as in FIG. 5, and the description is omitted. The sensor unit 2a includes a vibration detection sensor 21, a temperature detection sensor 22, a communication unit 23, and a second communication unit 24. The vibration detection sensor 21 and the temperature detection sensor 22 emit light downstream as a starting point.

The second communication unit 24 communicates with the monitoring unit 1. The communication unit 23 transmits information obtained from the vibration detection sensor 21, the temperature detection sensor 22, and the laser transmitter/receiver 3 (not shown in FIG. 6), and information received from the downstream sensor unit 2, to the second communication unit 24. The second communication unit 24 transmits those various pieces of information to the monitoring unit 1.

The vibration sensing sensor 21, the temperature detection sensor 22, the communication unit 23 and the second communication unit 24 are implemented, for example, by special circuits (hardware), respectively.

Figure 7:
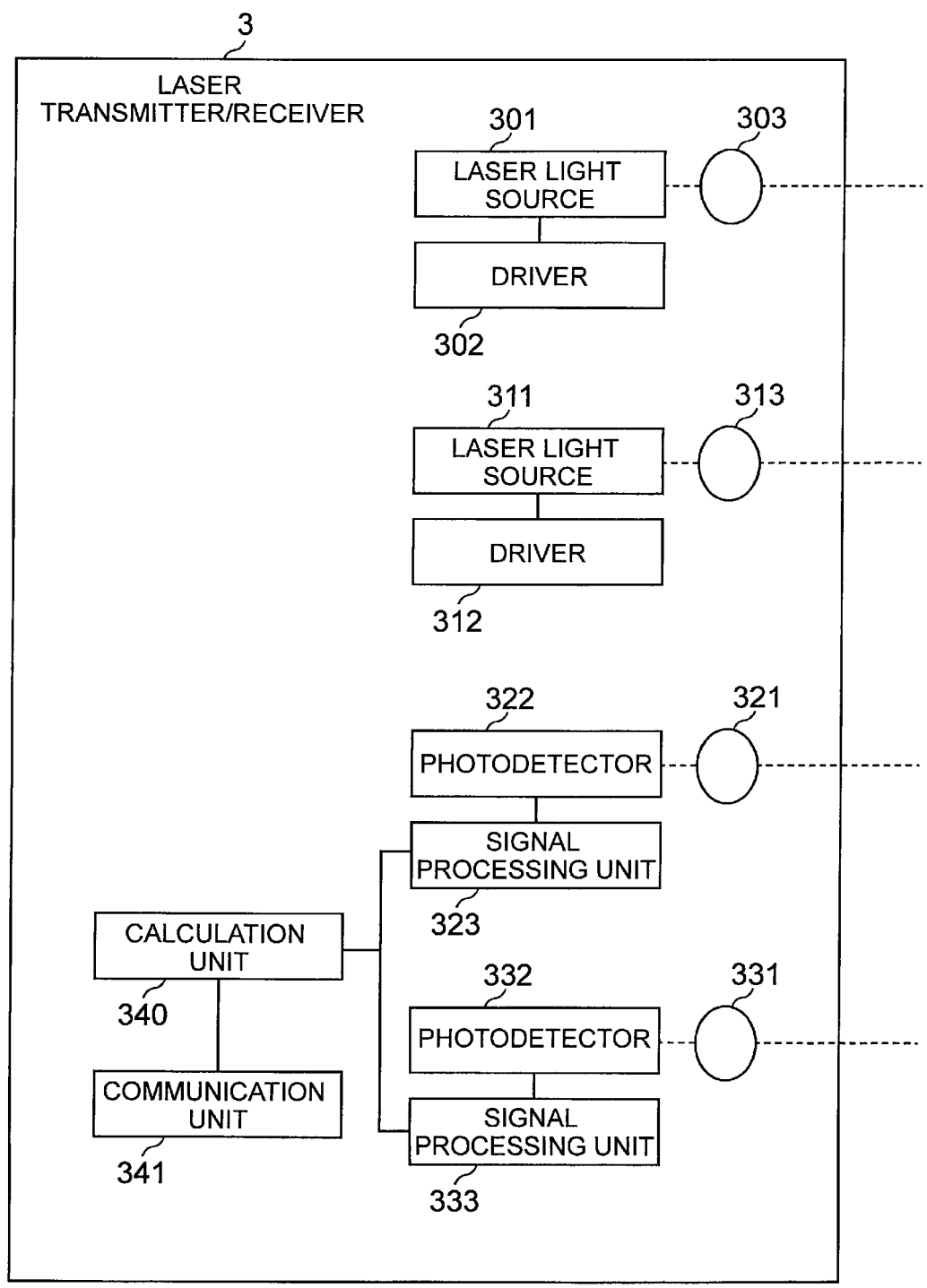
FIG. 7 It depicts a block diagram showing an example configuration of the laser transmitter/receiver.

FIG. 7 is a block diagram illustrating an example configuration of the laser transmitter/receiver 3. The reflector 4 (refer to FIG. 1), which is paired with the laser transmitter/receiver 3, is a reflector that reflects the optical signal transmitted by the laser transmitter/receiver 3 so as to return it to the laser transmitter/receiver 3.

The laser transmitter/receiver 3 includes two laser light sources 301, 311, drivers 302, 312 which drive the laser light sources 301, 311, and condensers 303, 313. Further, the laser transmitter/receiver 3 includes condensers 321, 331, photodetectors 322, 332, signal processing units 323, 333, a calculation unit 340, and a communication unit 341.

The driver 302 controls the drive current and temperature of the laser light source 301. The laser light source 301 outputs an optical signal of a predetermined wavelength (let's say $\lambda_1$ [μm]). The condenser 303 converts the optical signal into a collimated light and emits it into the atmosphere. The reflector 4 (refer to FIG. 1) reflects the optical signal to the laser transmitter/receiver 3 as a light source. When the optical signal is sent back to the laser transmitter/receiver 3, the optical signal is condensed by the condenser 321. The photodetector 322 converts the optical signal condensed by the condenser 321 into an electrical signal. The signal processing unit 323 calculates an average value of the concentration of CO between the laser transmitter/receiver 3 and the reflector 4 (refer to FIG. 1) from the electrical signal.

The driver 312 controls the drive current and temperature of the laser light source 311. The laser light source 311 outputs an optical signal of a predetermined wavelength (let's say $\lambda_2$ [μm]). The condenser 313 converts the optical signal into a collimated light and emits it into the atmosphere. The reflector 4 (refer to FIG. 1) reflects the optical signal to the laser transmitter/receiver 3 as a light source. When the optical signal is sent back to the laser transmitter/receiver 3, the optical signal is condensed by the condenser 331. The photodetector 332 converts the optical signal condensed by the condenser 331 into an electrical signal. The signal processing unit 333 calculates an average value of the concentration of $CO_2$ between the laser transmitter/receiver 3 and the reflector 4 (refer to FIG. 1) from the electrical signal.

The calculation unit 340 calculates the ratio of the average concentration of CO to the average concentration of $CO_2$. That is, the calculation unit 340 calculates the ratio of the concentration of CO to the concentration of $CO_2$ in the monitored section. Further, the calculation unit 340 determines whether the ratio is greater than the threshold T. When the calculation unit 340 determines that the ratio is greater than the threshold T, the calculation unit 340 causes the communication unit 341 to transmit information that the ratio of the concentration of CO to the concentration of $CO_2$ in the monitored section is greater than the threshold T and information indicating the monitored section assigned to the laser transmitter/receiver 3. The information indicating the monitored section is predetermined for each laser transmitter/receiver 3.

The communication unit 341 transmits the above information to the monitoring unit 1 via the sensor unit 2 connected to the laser transmitter/receiver 3, in accordance with an instruction of the calculation unit 340.

When the calculation unit 340 determines that the above ratio is less than or equal to the threshold T, the calculation unit 340 may not cause the communication unit 341 to transmit the above information.

The laser light sources 301, 311, the drivers 302, 312, the photodetectors 322, 332, the signal processing units 323, 333, the calculation unit 340, and the communication unit 341, for example, are implemented by special circuits (hardware), respectively.

Next, the process flow of the present exemplary embodiment will be described. The matters already described will be omitted appropriately.

Figure 8:
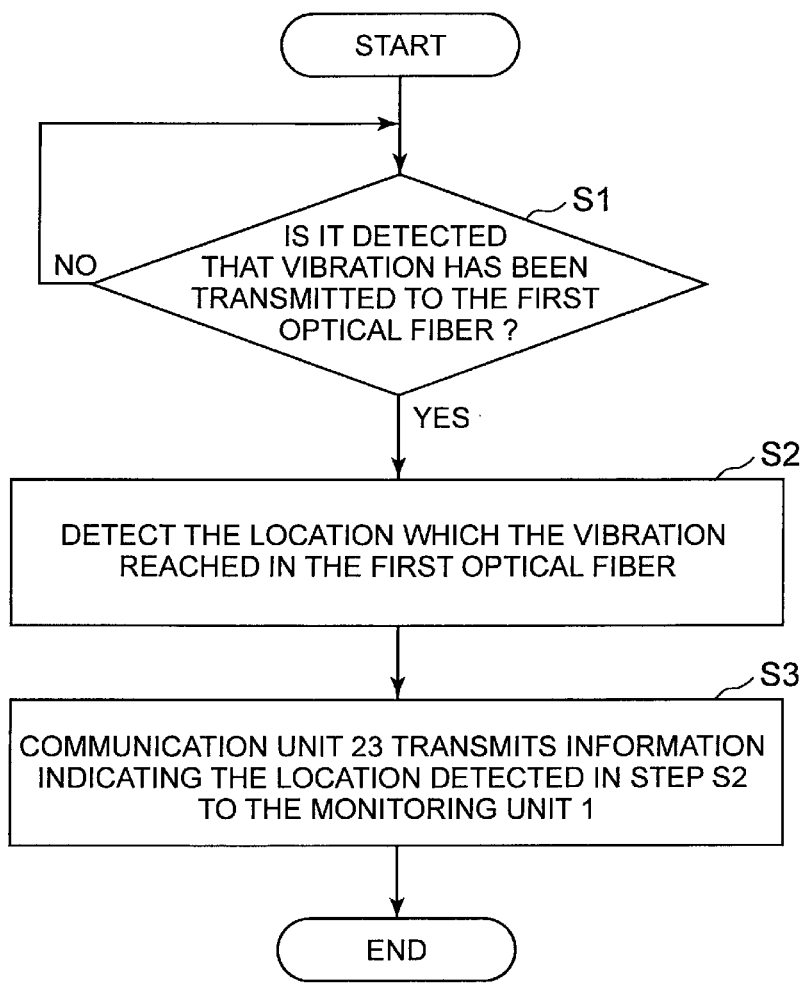
FIG. 8 It depicts a flowchart illustrating an example of a process flow when a vibration detection sensor detects a location which vibration reached in a first optical fiber.

FIG. 8 is a flowchart illustrating an example of a process flow when the vibration detection sensor 21 (refer to FIGS. 5 and 6) in the sensor unit 2 detects a location which the vibration reached in the first optical fiber 11.

The vibration detection sensor 21 determines whether or not it is detected that vibration transmitted to the first optical fiber 11 between the sensor unit 2 where the vibration detection sensor 21 is provided and the next sensor unit 2 at the downstream (step S1). When it has not detected that vibration was transmitted to the first optical fiber 11 (No in step S1), the vibration detection sensor 21 repeats the operation of step S1.

When it is detected that the vibration was transmitted to the first optical fiber 11 (Yes in step S1), the vibration detection sensor 21 detects the location which the vibration reached in the first optical fiber 11 (step S2). The vibration detection sensor 21 transmits information indicating the location to the communication unit 23.

The fact that the vibration was transmitted to the first optical fiber 11 means that an accident may have occurred in that vicinity.

The communication unit 23 transmits the information indicating the location detected in step S2 (the location where the vibration was transmitted in the first optical fiber 11) to the monitoring unit 1 (step S3).

Figure 9:
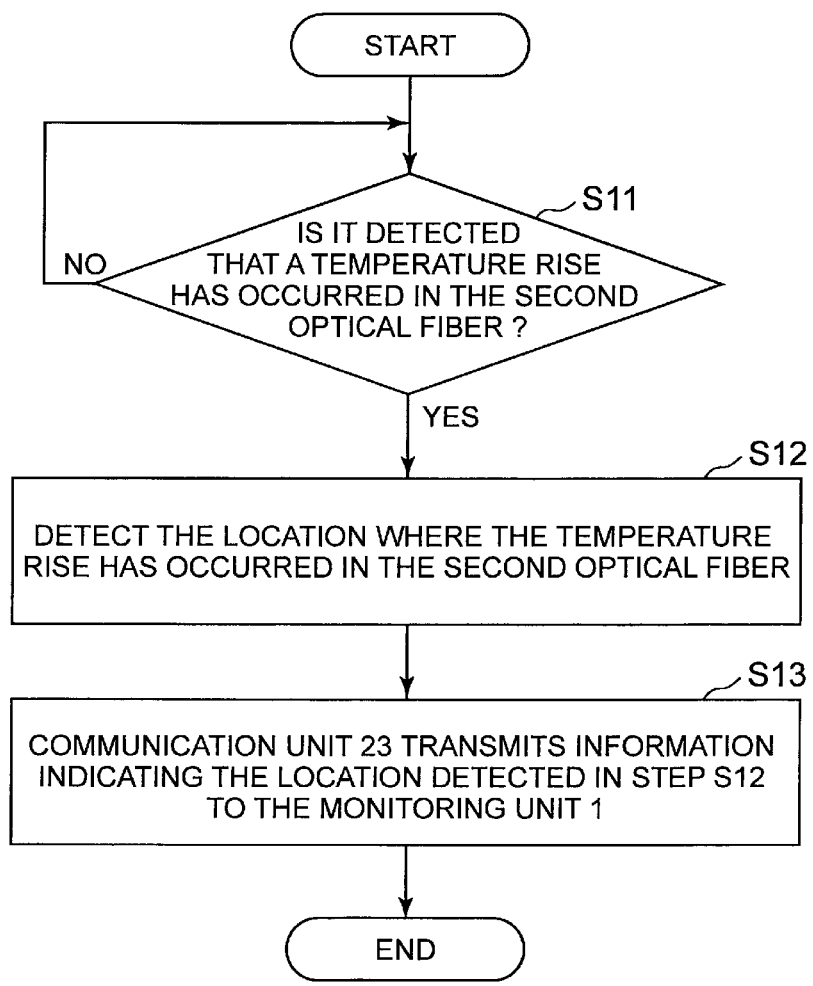
FIG. 9 It depicts a flowchart illustrating an example of a process flow when a temperature detection sensor detects a location where a temperature rise occurs in a second optical fiber.

FIG. 9 is a flowchart illustrating an example of a process flow when the temperature detection sensor 22 (refer to FIG. 5 and FIG. 6) in the sensor unit 2 detects a location where a temperature rise has occurred in the second optical fiber 12.

The temperature detection sensor 22 determines whether or not it is detected that a temperature rise has occurred at the second optical fiber 12 between the sensor unit 2 where the temperature detection sensor 22 is provided and the next sensor unit 2 at the downstream (step S11). When no temperature rise has occurred at the second optical fiber 12 (No in step S11), the temperature detection sensor 22 repeats the operation of step S11.

When it is detected that a temperature rise has occurred in the second optical fiber 12 (Yes in step S11), the temperature detection sensor 22 detects the location where the temperature rise has occurred in the second optical fiber 12 (step S12). The temperature detection sensor 22 transmits information indicating the location to the communication unit 23.

A temperature rise in the second optical fiber 12 means that a fire broke out in the vicinity.

The communication unit 23 transmits information indicating the location detected in step S12 (the location where the temperature rise occurred at the second optical fiber 12) to the monitoring unit 1 (step S13).

Figure 10:
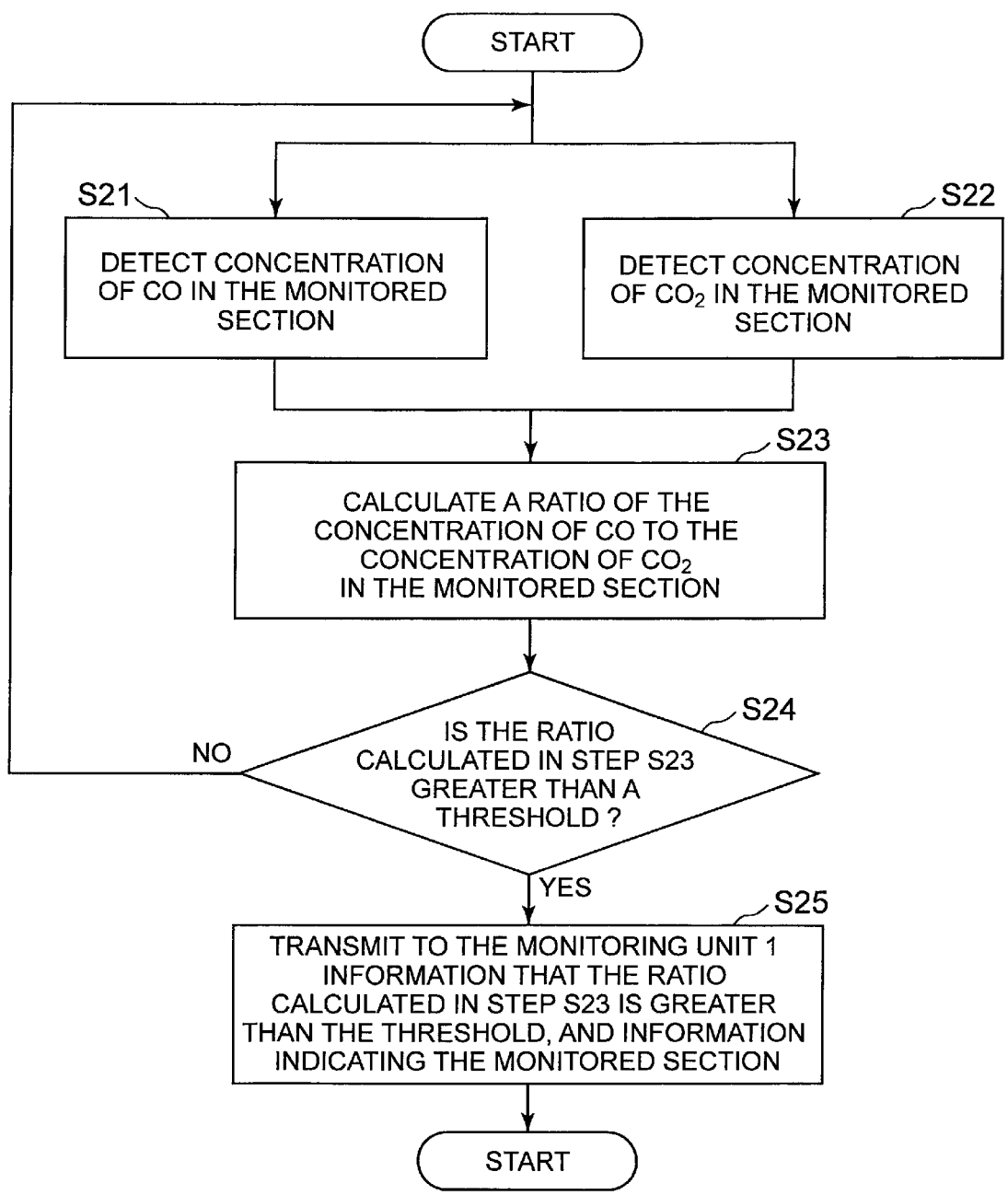
FIG. 10 It depicts a flowchart illustrating an example of a process flow when the laser transmitter/receiver derives the ratio of the concentration of CO to the concentration of $CO_2$ in the monitored section.

FIG. 10 is a flowchart showing an example of a process flow when the laser transmitter/receiver 3 derives the ratio of the concentration of CO to the concentration of $CO_2$ in the monitored section.

The laser transmitter/receiver 3 detects the concentration of CO in the monitored section assigned to the laser transmitter/receiver 3 (step S21). Specifically, the photodetector 332 converts the optical signal which is output from the laser light source 301 (refer to FIG. 7), reflected by the reflector 4 (refer to FIG. 1), and further condensed by the condenser 321 (refer to FIG. 7), into an electrical signal. The signal processing unit 323 then calculates the concentration of CO in the monitored section from the electrical signal.

The laser transmitter/receiver 3 detects the concentration of $CO_2$ in the monitored section assigned to the laser transmitter/receiver 3 (step S22). Specifically, the photodetector 332 converts the optical signal which is output from the laser light source 311 (refer to FIG. 7), reflected by the reflector 4 (refer to FIG. 1), and furthermore condensed by the condenser 331 (refer to FIG. 7), into an electrical signal. The signal processing unit 333 then calculates the concentration of $CO_2$ in the monitored section from the electrical signal.

The laser transmitter/receiver 3 may perform the operations of steps S21 and S22 in parallel. Alternatively, the laser transmitter/receiver 3 may perform the operations of steps S21 and S22 in a timed manner.

When the operation of steps S21 and S22 is performed on a time sharing basis, a laser light source that can change the frequency on a time sharing basis may be used. In this case, the number of laser light sources 301, 311, drivers 302, 312, collectors 303, 313, condensers 321, 331, photodetectors 322, 332, and signal processing units 323, 333 can be reduced to half.

After performing steps S21 and S22, the calculation unit 340 (refer to FIG. 7) calculates the ratio of the concentration of CO to the concentration of $CO_2$ in the monitored section (step S23).

Next, the calculation unit 340 determines whether the ratio (the ratio of the concentration of CO to the concentration of $CO_2$ in the monitored section) calculated in step S23 is greater than the threshold T (step S24).

When the ratio calculated in step S23 is less than or equal to the threshold T (No in step S24), the laser transmitter/receiver 3 repeats the operation from steps S21, S22 and thereafter.

When the ratio calculated in step S23 is greater than the threshold T (Yes in step S24), the calculation unit 340 causes the communication unit 341 to transmit information that the ratio of the concentration of CO to the concentration of $CO_2$ in the monitored section is greater than the threshold T, and information indicating the monitored section assigned to the laser transmitter/receiver 3. The communication unit 341 transmits the information to the monitoring unit 1 via the sensor unit 2 connected to the laser transmitter/receiver 3 in accordance with an instruction of the calculation unit 340 (step S25).

Figure 11:
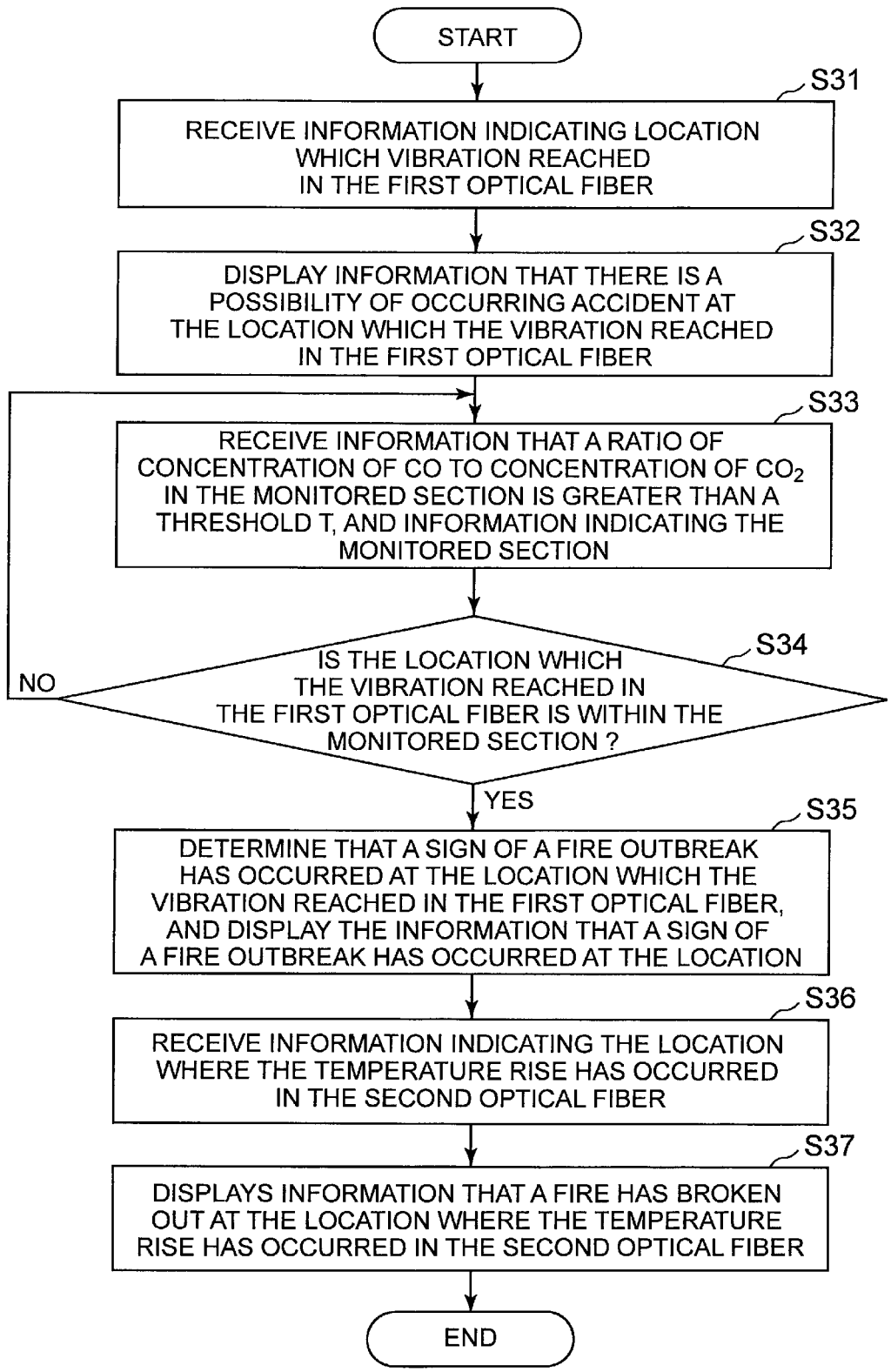
FIG. 11 It depicts a flowchart illustrating an example of a processing process of the monitoring unit.

FIG. 11 is a flowchart showing an example of a progress flow of the monitoring unit 1.

The monitoring unit 1 first receives the information indicating the location from the sensor unit 2, which detects the location which the vibration reached in the first optical fiber 11 (step S31).

The monitoring unit 1 then displays the information on the display that there is a possibility of occurring accident at the location which the vibration reached in the first optical fiber 11 (step S32).

Figure 12:
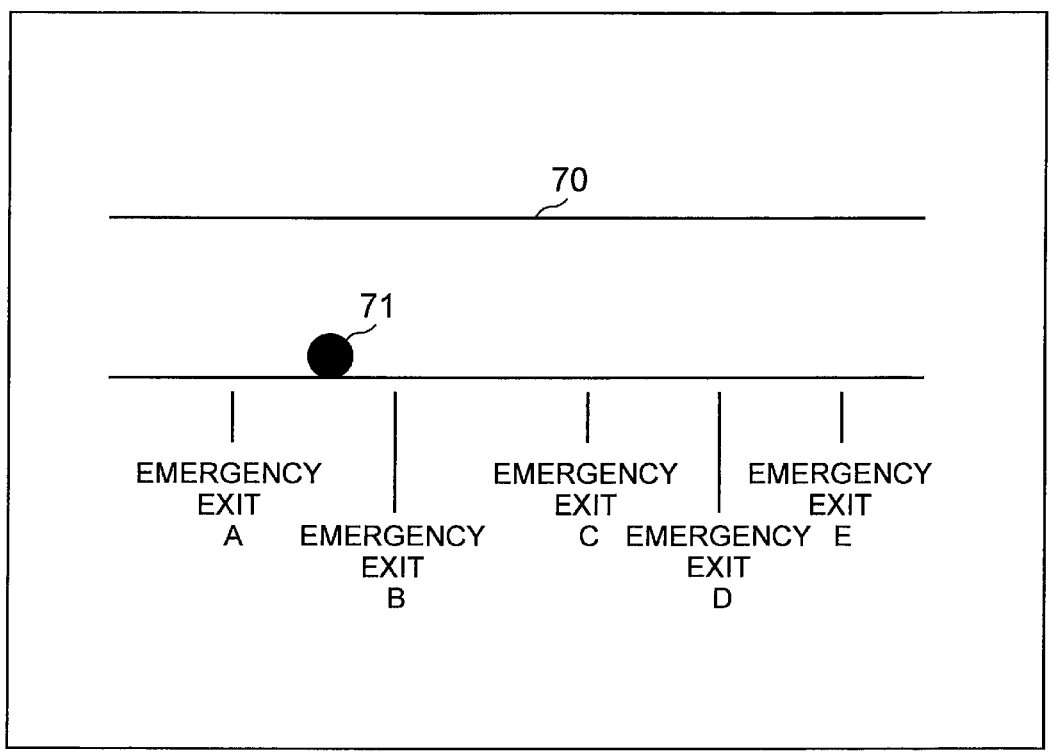
FIG. 12 It depicts a schematic diagram showing an example of a display screen of information indicating that an accident may have occurred at a location which vibration reached in the first optical fiber.

FIG. 12 is a schematic diagram showing an example of a display screen of information indicating that an accident may have occurred at a location which the vibration reached in the first optical fiber 11. The monitoring unit 1 may, for example, schematically display a tunnel 70 in the screen and display an icon 71 in the tunnel 70 at a position corresponding to the location where the vibration was transmitted in the first optical fiber 11, thereby displaying that there is a possibility of occurring an accident at the location. For example, the monitoring unit 1 may display the icon 71 and display a string of text such as "Accident may have occurred" in the vicinity of the icon 71. FIG. 12 illustrates a case in which the location of each emergency exit in the tunnel 70 is also schematically displayed. FIG. 12 is an example of a display screen. However, the display screen is not limited to the example shown in FIG. 12.

The operator who confirms the information displayed in step S32 confirms, for example, the situation of the actual location in the tunnel corresponding to the displayed portion of icon 71, for example, with the image of the camera.

Subsequently, the laser transmitter/receiver 3, which determines that the ratio of the concentration of CO to the concentration of $CO_2$ in the monitored section is greater than the threshold T, transmits to the monitoring unit 1 the information that the ratio of the concentration of CO to the concentration of $CO_2$ in the monitored section is greater than the threshold T and the information indicating the monitored section, and the monitoring unit 1 receives the information (step S33).

After performing step S33, the monitoring unit 1 determines whether the location which the vibration reached in the first optical fiber 11 is within the monitored section indicated by the information received in step S33 (step S34).

In general, a sign of a fire outbreak (in this example, the ratio of the concentration of CO to the concentration of $CO_2$ is greater than the threshold T) occurs at the location where the accident occurred. Therefore, it is generally conceivable that in step S33, the location where the vibration was transmitted in the first optical fiber 11 is often determined to be within the monitored section.

When the location where the vibration was transmitted in the first optical fiber 11 is not within the monitored section (No in step S34), the monitoring unit 1 waits that information that the ratio of the concentration of CO to the concentration of $CO_2$ in the monitored section is greater than the threshold T and information indicating the monitored section are sent, and when the information is sent, the monitoring unit 1 repeats the operation from step S33 and thereafter. When the location which the vibration reached in the first optical fiber 11 is not within the monitored section, the monitoring unit 1 may display the monitored section on the display, and the operator may check the actual situation of the section with the image of the camera or the like.

When the location which the vibration reached in the first optical fiber 11 is within the monitored section (Yes in step S34), the monitoring unit 1 determines that a sign of a fire outbreak has occurred at the location which the vibration reached in the first optical fiber 11, and displays on the display the information that a sign of a fire outbreak has occurred at the location (step S35). For example, the monitoring unit 1 may notify the operator that a sign of a fire outbreak has occurred at the location which the vibration reached in the first optical fiber 11 by flashing the icon 71 in the screen illustrated in FIG. 12. For example, the monitoring unit 1 may display a string of text such as "There is a sign of a fire outbreak" near the icon 71.

After confirming the information displayed in step S35, the operator performs traffic control and evacuation guidance in the tunnel based on the location where a sign of a fire outbreak occurs.

If a fire breaks out at the location of the accident after a sign of a fire has occurred, the sensor unit 2, which transmitted the information in step S31, detects that a temperature rise has occurred in the second optical fiber 12 and further detects the location where the temperature rise has occurred in the second optical fiber 12. The sensor unit 2 transmits information indicating the location where the temperature rise has occurred in the second optical fiber 12 to the monitoring unit 1, and the monitoring unit 1 receives the information (step S36).

After performing step S36, the monitoring unit 1 displays information on the display that a fire has broken out at the location where a temperature rise has occurred in the second optical fiber 12 (step S37). For example, the monitoring unit 1 may indicate that a fire has broken out at the location by displaying an icon in the screen illustrated in FIG. 12 at a position corresponding to the location where the temperature rise has occurred in the second optical fiber 12, thereby displaying that a fire has broken out at the location. The fact that the fire broke out at the point where the accident occurred means that the location which the vibration reached in the first optical fiber 11 and the location where the temperature rise occurred in the second optical fiber 12 are almost at the same location. Accordingly, if the position of the screen corresponding to the location where the temperature rise occurred in the second optical fiber 12 is approximately at the same location as the display portion of the icon 71, the monitoring unit 1 may indicate that a fire has broken out at the location, for example, by changing the color of the icon 71. For example, the monitoring unit 1 may display a string of text such as "A fire has broken out" near the icon 71.

After reviewing the information displayed in step S37, the operator continues to regulate traffic and guide evacuation in the tunnel based on the location where the fire broke out.

According to the present exemplary embodiment, the monitoring unit 1 first receives information indicating the location which the vibration reached in the first optical fiber 11, and then receives information indicating that the ratio of the concentration of CO to the concentration of $CO_2$ in the monitored section is greater than the threshold T, and information indicating the monitored section. Accordingly, the monitoring unit 1 is able to identify the location where a sign of a fire outbreak occurred as the same location which the vibration reached in the first optical fiber 11, because the location is within the monitored section. The monitoring unit 1 can then specifically display on the display the location where a sign of a fire outbreak has occurred, and can communicate the location to the operator.

Therefore, according to the first exemplary embodiment, it is possible to detect locations early where there is a possibility of fire outbreak.

In the first exemplary embodiment, it can be said that steps S36, S37 (refer to FIG. 11) are a process for communicating to the operator that a fire has actually broke out, after communicating to the operator the location where a sign of a fire outbreak has occurred. By teaching to the operator the location where a sign of a fire outbreak has occurred, the operator can begin to take action such as traffic control and evacuation guidance. Accordingly, in the first exemplary embodiment, the monitoring unit 1 may terminate the process at step S35 and not perform the operations of steps S36 and S37. In that case, each sensor unit 2 may not include a temperature detection sensor 22 (refer to FIG. 5 and FIG. 6), and the second optical fiber 12 may not be provided. Even in this case, the monitoring unit 1 can identify a location where a sign of a fire outbreak has occurred and inform the operator of the location.

In the first exemplary embodiment, a first optical fiber 11 for detecting the occurrence of vibrations based on an accident and the location thereof, and a second optical fiber 12 for detecting the temperature rise due to a fire outbreak and the location where the temperature rise has occurred may be common to a single optical fiber. In other words, the sensor unit 2 may use a single optical fiber to detect the occurrence of vibration and the location where the vibration occurs, and to detect the temperature rise and the location where the temperature rise has occurred. In this case, the sensor unit 2 may include one sensor having the functions of the vibration detection sensor 21 and the temperature detection sensor 22 instead of the vibration detection sensor 21 and the temperature detection sensor 22. The sensor may then use a single optical fiber to detect the occurrence of the vibration and the location where the vibration occurs, and to detect the temperature rise and the location where the temperature rise occurs.

Exemplary Embodiment 2

Figure 13:
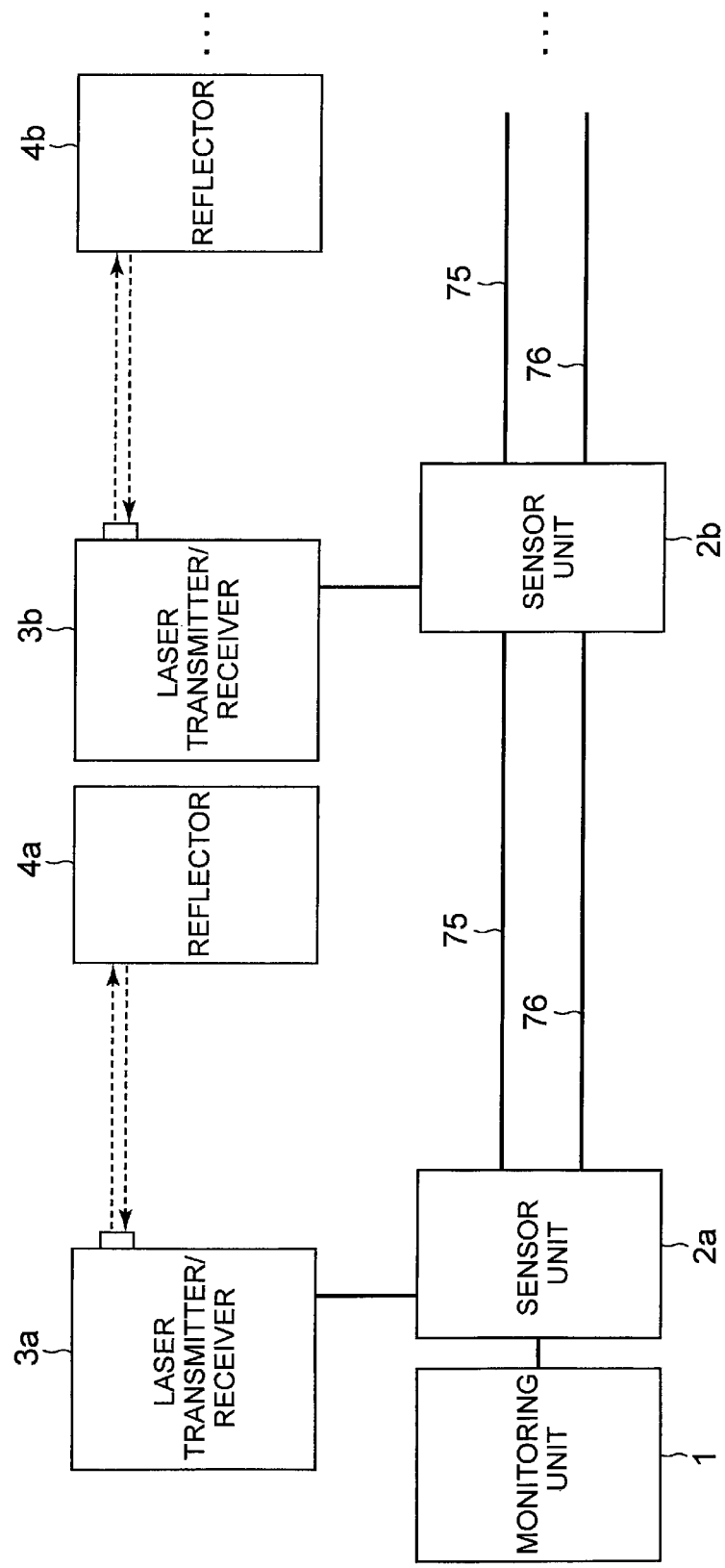
FIG. 13 It depicts a block diagram illustrating an example of a fire detection system in a second exemplary embodiment of the present invention.

A second exemplary embodiment of the present invention will be described below. The same matters as in the first exemplary embodiment will be omitted appropriately. FIG. 13 is a block diagram illustrating an example of a fire detection system of the second exemplary embodiment of the present invention.

In the second exemplary embodiment, the optical fiber (e.g., the first optical fiber 11 in the first exemplary embodiment) used for detecting the occurrence of vibration based on an accident and the location where the vibration occurs may not be provided. In the second exemplary embodiment, an optical fiber (e.g., the second optical fiber 12 in the first exemplary embodiment) used for detecting the temperature rise due to the occurrence of a fire outbreak and the location where the temperature rise has occurred, and an optical fiber (e.g., the third optical fiber 13 in the first exemplary embodiment) used for transmitting various information to the monitoring unit 1 is provided.

In the second exemplary embodiment, for convenience, "an optical fiber used for detecting a temperature rise due to a fire outbreak or a location where the temperature rise has occurred" is referred to as "first optical fiber 75" and "an optical fiber used for transmitting various information to the monitoring unit 1" is referred to as "second optical fiber 76". The "first optical fiber 75" in the second exemplary embodiment corresponds to the "second optical fiber 12" in the first exemplary embodiment. The "second optical fiber 76" in the second exemplary embodiment corresponds to the "third optical fiber 13" in the first exemplary embodiment.

The fire detection system of the second exemplary embodiment comprises a monitoring unit 1, a plurality of sensor units 2, and a plurality of pairs of a laser transmitter/receiver 3 and a reflectors 4.

A plurality of sensor units 2 are provided to pass through a first optical fiber 75 and a second optical fiber 76.

The laser transmitter/receiver 3 and the reflector 4 are the same as the laser transmitter/receiver 3 and the reflector 4 in the first exemplary embodiment. As in the first exemplary embodiment, each laser transmitter/receiver 3 is communicably connected to the corresponding sensor units 2.

In the example shown in FIG. 13, the sensor unit 2a, which is communicably connected to the monitoring unit 1, is the most upstream sensor, and other sensor units 2 (such as the sensor unit 2b) are sequentially arranged in a downstream side. As already described, a plurality of sensor units 2 may be connected in a looped manner.

Each sensor unit 2 emits light to the first optical fiber 75, and when a location where a temperature rise has occurred in the first optical fiber 75 is detected between the sensor unit 2 and the next sensor unit 2 at the downstream side, information indicating the location is transmitted to the sensor unit 2a at the most upstream side, using the second optical fiber 76. The sensor unit 2a transmits the information indicating the location to the monitoring unit 1.

The monitoring unit 1 is the same as the monitoring unit 1 in the first exemplary embodiment, and receives information transmitted by the laser transmitter/receiver 3 and the sensor unit 2, and outputs various information based on the received information.

The monitoring unit 1 receives information indicating the state of gas and the monitored section from the laser transmitter/receiver 3, and when the state of gas meets a predetermined condition (in this example, the condition that the ratio of the concentration of CO to the concentration of $CO_2$ in the monitored section is greater than a threshold T), the monitoring unit 1 displays information on the display that a sign of a fire outbreak has occurred in that monitored section.

When the monitoring unit 1 receives information from the sensor unit 2, which detects a temperature rise in the first optical fiber 75, of the location where the temperature rise occurred in the first optical fiber 75, the monitoring unit 1 displays information on the display that a fire has broken out at the location.

Figure 14:
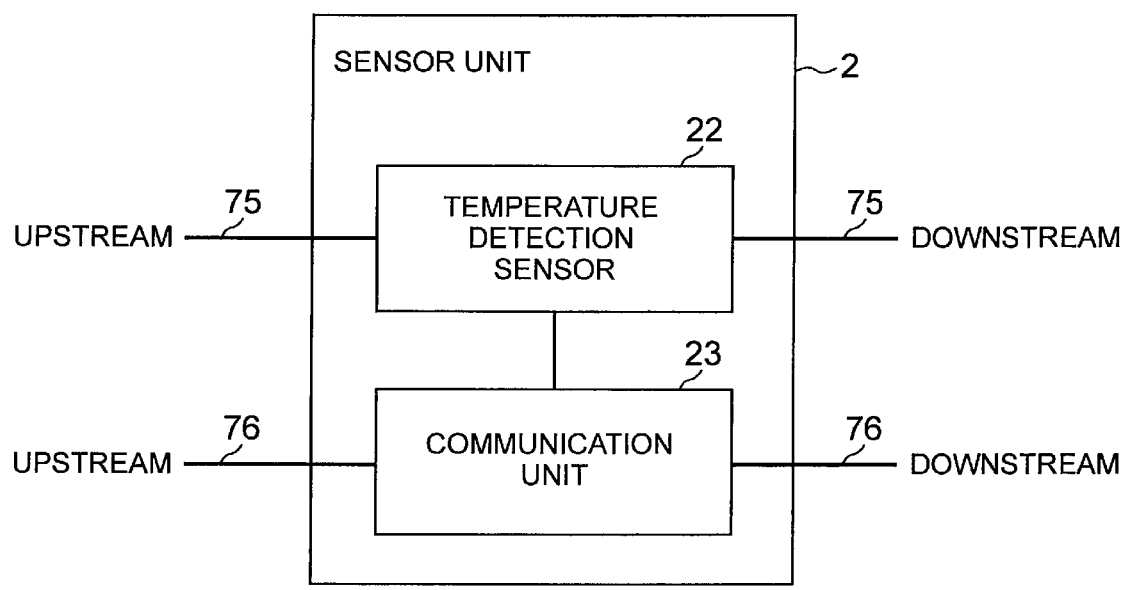
FIG. 14 It depicts a block diagram showing an example configuration of a sensor unit of the second exemplary embodiment.

FIG. 14 is a block diagram showing an example of a configuration of the sensor unit 2 of the second exemplary embodiment. Elements identical to the elements of the sensor unit 2 of the first exemplary embodiment are marked with the same sign as in FIG. 5, and the description is omitted. The sensor unit 2 of the second exemplary embodiment is similar to the sensor unit 2 of the first exemplary embodiment, except that the vibration detection sensor 21 (refer to FIG. 5) in the first exemplary embodiment is not provided. The temperature detection sensor 22 and the communication unit 23 are the same as the temperature detection sensor 22 and the communication unit 23 in the first exemplary embodiment.

Figure 15:
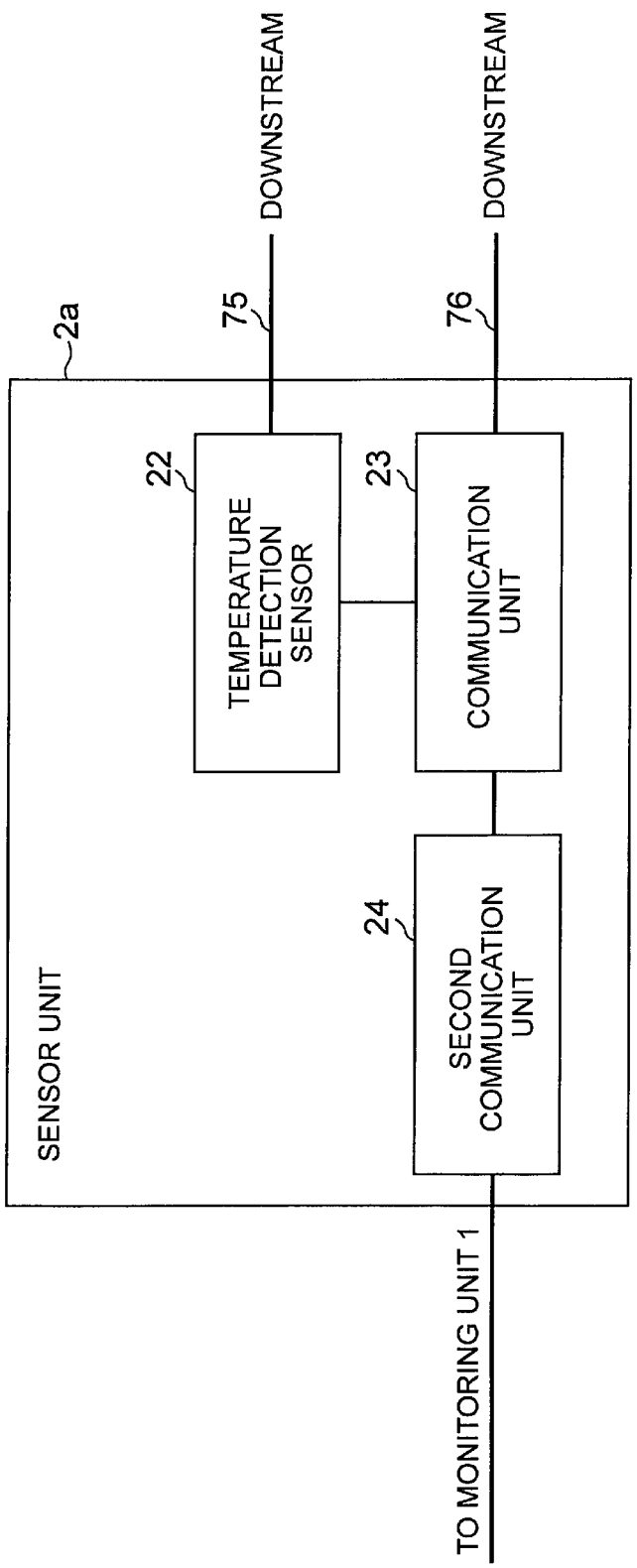
FIG. 15 It depicts a block diagram showing an example configuration of a sensor unit connected to a monitoring unit in the second exemplary embodiment.

FIG. 15 is a block diagram showing an example configuration of the sensor unit 2a at the most upstream side (sensor unit 2a connected to the monitoring unit 1) in the second exemplary embodiment. Elements similar to those shown in FIG. 6 are marked with the same sign as in FIG. 6, and the description is omitted. The sensor unit 2a in the second exemplary embodiment is similar to the sensor unit 2a in the first exemplary embodiment, except that the vibration detection sensor 21 (refer to FIG. 6) in the first exemplary embodiment is not provided. The temperature detection sensor 22, the communication unit 23 and the second communication unit 24 are the same as the temperature detection sensor 22, the communication unit 23 and the second communication unit 24 in the first exemplary embodiment.

As mentioned above, the laser transmitter/receiver 3 and reflector 4 are the same as the laser transmitter/receiver 3 and reflector 4 in the first exemplary embodiment. The configuration of the laser transmitter/receiver 3 is the same as the configuration of the laser transmitter/receiver 3 in the first exemplary embodiment (refer to FIG. 7) and will not be described.

The process flow when the temperature detection sensor 22 in the sensor unit 2 detects a location where a temperature rise has occurred in the first optical fiber 75 is the same as the process flow in the first exemplary embodiment (refer to FIG. 9).

The process flow when the laser transmitter/receiver 3 derives the ratio of the concentration of CO to the concentration of $CO_2$ in the monitored section is also the same as the process flow in the first exemplary embodiment (refer to FIG. 10).

Figure 16:
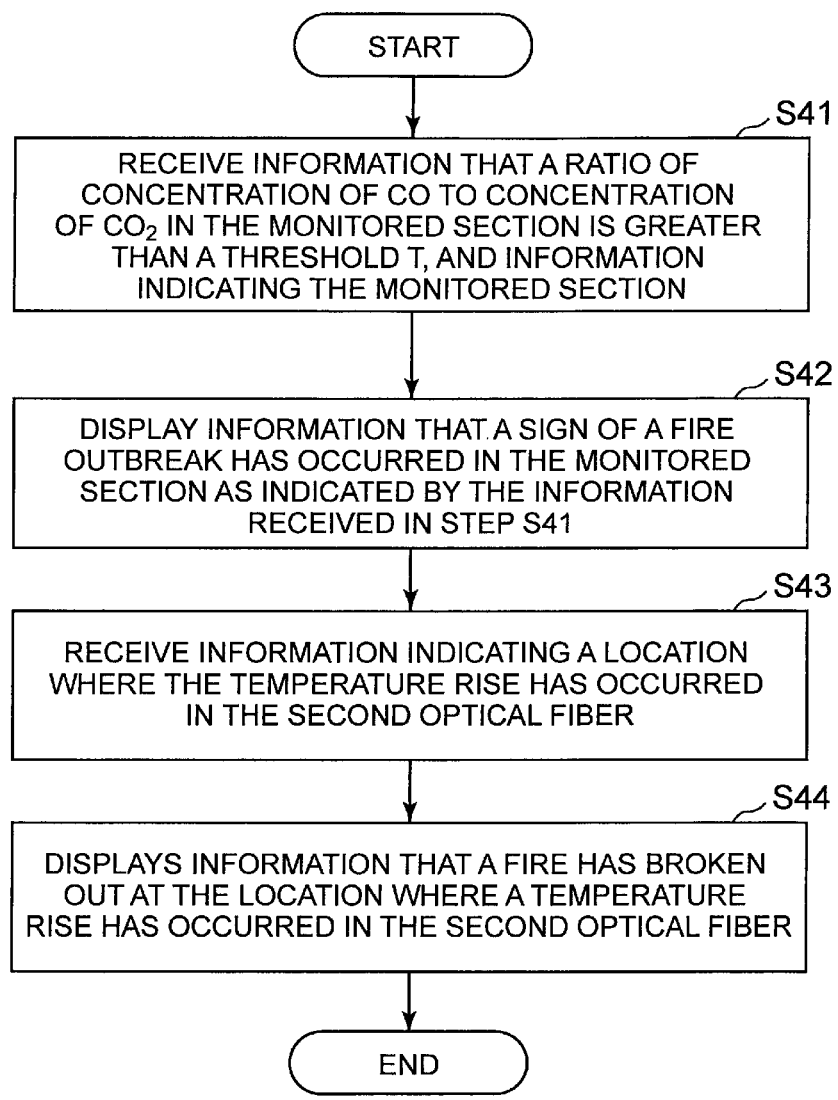
FIG. 16 It depicts a flowchart illustrating an example of a process flow of the monitoring unit in the second exemplary embodiment.

FIG. 16 is a flowchart illustrating an example of a process flow of the monitoring unit 1 in the second exemplary embodiment.

The laser transmitter/receiver 3, which determines that the ratio of the concentration of CO to the concentration of $CO_2$ in the monitored section is greater than the threshold T, transmits to the monitoring unit 1 information that the ratio of the concentration of CO to the concentration of $CO_2$ in the monitored section is greater than the threshold T and information indicating the monitored section, and the monitoring unit 1 receives the information (step S41).

Figure 17:
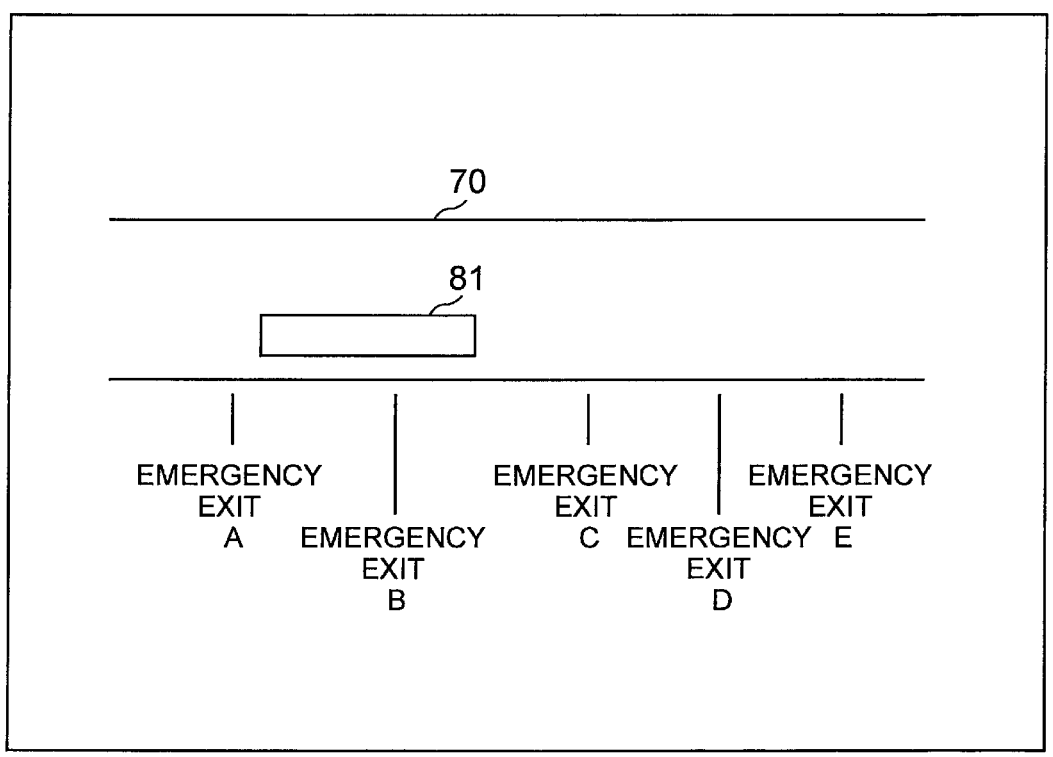
FIG. 17 It depicts a schematic diagram showing an example of a display screen of information indicating that a sign of a fire outbreak has occurred in a monitored section.

Next, the monitoring unit 1 displays on the display (step S42) information that a sign of a fire outbreak has occurred in the monitored section, as indicated by the information received in step S41. FIG. 17 is a schematic diagram showing an example of a display screen of information indicating that a sign of a fire outbreak has occurred in the monitored section. The monitoring unit 1 schematically displays a tunnel 70 on the screen, for example, and displays an icon 81, in the form of a band, in a position corresponding to the monitored section in the tunnel indicated by the information received in step S41. By displaying the icon 81, the monitoring unit 1 indicates that a sign of a fire outbreak has occurred in that section. FIG. 17 illustrates locations of emergency exits in the tunnel 70 is also displayed in a schematic manner. FIG. 17 is an example of a display screen. The display screen is not limited to the example shown in FIG. 17.

The operator who confirms the information displayed in step S42, for example, confirms the situation of the actual section of the tunnel corresponding to the displayed portion of icon 81 with the image of the camera and so on, and performs traffic control and evacuation guidance in the tunnel.

If a fire breaks out at any location in the monitored section after occurring a sign of a fire outbreak, the sensor unit 2 at the upstream of the fire location detects that a temperature rise has occurred in the first optical fiber 75, and furthermore detects the location where the temperature rise has occurred in the first optical fiber 75. The sensor unit 2 transmits information indicating the location where the temperature rise has occurred in the first optical fiber 75 to the monitoring unit 1, and the monitoring unit 1 receives the information (step S43).

Figure 18:
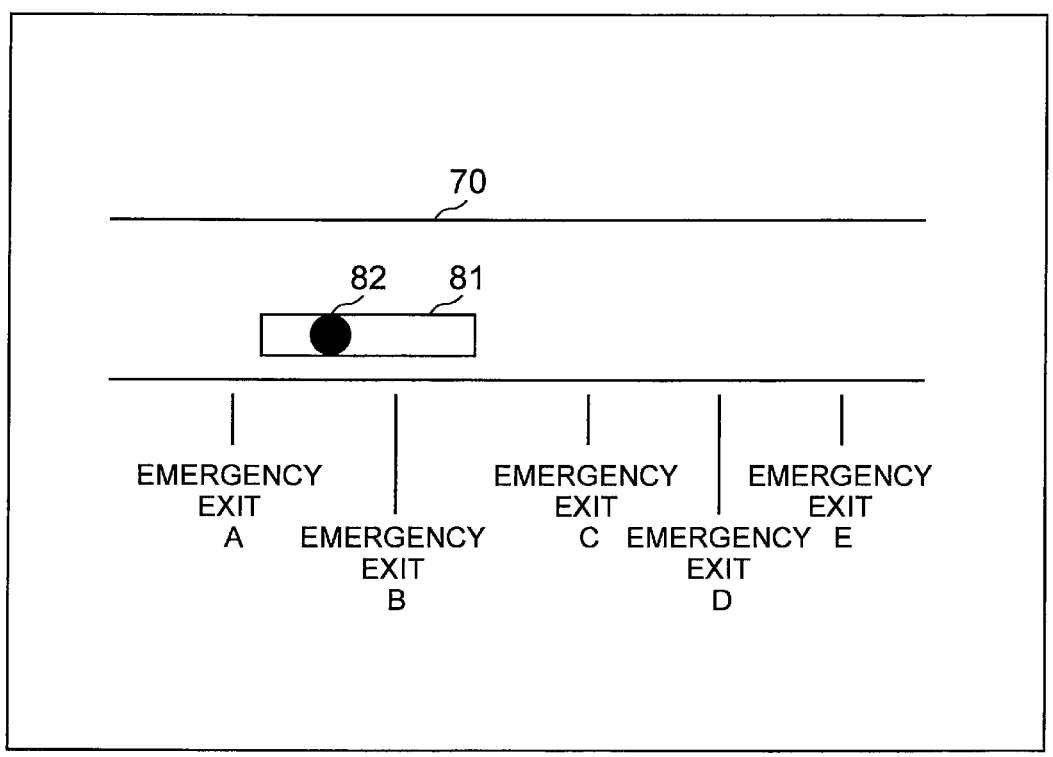
FIG. 18 It depicts a schematic diagram showing an example of a screen displayed in step S44.

After performing step S43, the monitoring unit 1 displays information on the display (step S44) that a fire has broken out at the location where a temperature rise has occurred in the first optical fiber 75 (step S44). FIG. 18 is a schematic diagram showing an example of the screen displayed in step S44. The monitoring unit 1 may, for example, display that a fire has occurred at the location in the screen shown in FIG. 17 by superimposing an icon 82 on a portion of the screen corresponding to the location where the temperature rise has occurred at the first optical fiber 75, thereby displaying that a fire has broken out at the location.

In the second exemplary embodiment, the location where a sign of a fire outbreak occurred is indicated as a section (refer to FIG. 17). Subsequently, in step S44, the location where the fire has broken is specifically indicated (refer to FIG. 18). Based on the information displayed in step S44, the operator identifies a more specific location than the wide section, and more accurately performs traffic control and evacuation guidance in the tunnel according to the location.

According to the second exemplary embodiment, it is possible to detect a section of a possible fire outbreak before the detection of a fire outbreak location at an early stage.

Next, modifications of each of the above exemplary embodiments will be described.

In the first exemplary embodiment and the second exemplary embodiment, each laser transmitter/receiver 3 comprises a calculation unit 340 (refer to FIG. 7) that calculates the ratio of the concentration of CO to the concentration of $CO_2$ in the monitored section and determines whether the ratio is greater than a threshold T. The monitoring unit 1 may have a function for calculating the ratio of the concentration of CO to the concentration of $CO_2$ in the monitored section and determining whether the ratio is greater than the threshold T.

In this case, the communication unit 341 (refer to FIG. 7) of each laser transmitter/receiver 3 transmits the concentration of CO and the concentration of $CO_2$ and information indicating the monitored section each time the concentration of CO and the concentration of $CO_2$ in the monitored section are calculated to the monitoring unit 1 via the sensor unit 2 connected to the laser transmitter/receiver 3.

In the first exemplary embodiment, the monitoring unit 1 first receives from the sensor unit 2 information indicating a location which the vibration reached in the first optical fiber 11. In this modification applied to the first exemplary embodiment, the monitoring unit 1 receives from the laser transmitter/receiver 3 the concentration of CO and the concentration of $CO_2$ and information indicating the monitored section. Then, the monitoring unit 1 determines whether the location which the vibration reached in the first optical fiber 11 is within the monitored section. The monitoring unit 1 calculates the ratio of the concentration of CO to the concentration of $CO_2$, and determines whether the ratio is greater than the threshold T. When the location which the vibration reached in the first optical fiber 11 is within the monitored section and the above ratio is greater than the threshold T, the monitoring unit 1 may determine that a sign of a fire outbreak has occurred at the location. The other matters are the same as in the first exemplary embodiment.

In this modification applied to the second exemplary embodiment, the monitoring unit 1 also receives the concentration of CO and the concentration of $CO_2$ and information indicating the monitored section from the laser transmitter/receiver 3. In this case, the monitoring unit 1 calculates the ratio of the concentration of CO to the concentration of $CO_2$ and determines whether the ratio is greater than the threshold T. Then, when the ratio of the concentration of CO to the concentration of $CO_2$ is greater than the threshold T, the monitoring unit 1 may display on the display the information that a sign of a fire outbreak has occurred in the monitored section. The other matters are the same as in the second exemplary embodiment.

Next, other modifications of each of the above exemplary embodiments will be described.

In each of the above exemplary embodiments, a case was shown where such an event as the ratio of the concentration of CO to the concentration of $CO_2$ is greater than a threshold is used as an event that means that a sign of a fire outbreak has occurred within the monitored section. As already mentioned, the event that indicates the occurrence of a sign of a fire outbreak in the monitored section is not limited to such an event. That is, the event that the ratio of the concentration of CO to the concentration of $CO_2$ is greater than a threshold is an example of an event that means that a sign of a fire outbreak has occurred within the monitored section. For example, each exemplary embodiment of the present invention may utilize the event that a pattern of changes in the ratio of the concentration of CO to the concentration of $CO_2$ shows a predetermined pattern as an event signifying that a sign of a fire outbreak has occurred within the monitored section.

For example, in each exemplary embodiment, the calculation unit 340 (refer to FIG. 7) of the laser transmitter/receiver 3 may periodically calculate an average value of the concentration of CO in the monitored section and an average value of the concentration of $CO_2$ in the monitored section, and the calculation unit 340 may calculate the ratio of the average value of the concentration of CO to the average value of the concentration of $CO_2$ in the monitored section for each calculation of the average value of the concentration of CO and the average value of the concentration of $CO_2$. In other words, the calculation unit 340 of the laser transmitter/receiver 3 may periodically calculate the ratio of the concentration of CO to the concentration of $CO_2$ in the monitored section. As a result, the calculation unit 340 obtains time series data of the ratio of the concentration of CO to the concentration of $CO_2$ in the monitored section. When a pattern of changes in the ratio of the concentration of CO to the concentration of $CO_2$ in this time series data shows a predetermined pattern that is predetermined, the calculation unit 340 may cause the communication unit 341 (refer to FIG. 7) to transmit information that the pattern of changes in the ratio of the concentration of CO to the concentration of $CO_2$ shows a predetermined pattern, and information indicating the monitored section assigns to the laser transmitter/receiver 3. The communication unit 341 transmits the above information to the monitoring unit 1 via the sensor unit 2 connected to the laser transmitter/receiver 3, in accordance with an instruction of the calculation unit 340.

In this modification applied to the first exemplary embodiment, when the monitoring unit 1 receives information indicating that a pattern of changes in the ratio of CO concentration to $CO_2$ concentration shows a predetermined pattern, and information indicating the monitored section assigned to the laser transmitter/receiver 3, the monitoring unit 1 determines whether or not the location which the vibration reached in the first optical fiber 11 (refer to FIG. 1, etc.) is within the monitored section. When the location which the vibration reached in the first optical fiber 11 is within the monitored section, the monitoring unit 1 determines that a sign of a fire outbreak has occurred at the location, and displays the information that a sign of a fire outbreak has been multiplied at the location, on the display.

In this modification applied to the second exemplary embodiment, when the monitoring unit 1 receives information indicating that a pattern of changes in the ratio of the concentration of CO to the concentration of $CO_2$ shows a predetermined pattern and information indicating the monitored section assigned to the laser transmitter/receiver 3, the monitoring unit 1 displays on the display the information that a sign of a fire outbreak has occurred in the monitored section.

The monitoring unit 1 may also perform a determination of whether a pattern of changes in the ratio of the concentration of CO to the concentration of $CO_2$ shows a predetermined pattern that is predetermined. In this case, the calculation unit 340 of each laser transmitter/receiver 3 periodically calculates the concentration of CO and the concentration of $CO_2$ in the monitored section. The communication unit 341 of each laser transmitter/receiver 3 periodically transmits information indicating the concentration of CO, the concentration of $CO_2$, and the monitored section assigned to the laser transmitter/receiver 3 to the monitoring unit 1, via the sensor unit 2 connected to the laser transmitter/receiver 3.

The monitoring unit 1 periodically receives from each laser transmitter/receiver 3 the information indicating the concentration of CO, the concentration of $CO_2$ in the monitored section assigned to the laser transmitter/receiver 3, and the monitored section. The monitoring unit 1 calculates the ratio of the concentration of CO to the concentration of $CO_2$ in the monitored section for each laser transmitter/receiver 3, which is the source of the information, to generate the time series data. The monitoring unit 1 identifies the monitored section assigned to the laser transmitter/receiver 3, which is the source of the concentration of CO and the concentration of $CO_2$, when a pattern of the change in the ratio of the concentration of CO to the concentration of $CO_2$ in the time series data shows a predetermined pattern that is predetermined. That is, the monitoring unit 1 identifies a monitored section in which the pattern of changes in the ratio of the concentration of CO to the concentration of $CO_2$ shows a predetermined pattern.

In this modification applied to the first exemplary embodiment, the monitoring unit 1 determines whether the location which the vibration reached in the first optical fiber 11 (refer to FIG. 1, etc.) is within a monitored section in which a pattern of changes in the ratio of the concentration of CO to the concentration of $CO_2$ shows a predetermined pattern. When the location which the vibration reached in the first optical fiber 11 is within the monitored section, the monitoring unit 1 determines that a sign of a fire outbreak has occurred at the location, and displays the information that a sign of a fire outbreak has been multiplied at the location, on the display.

In this modification applied to the second exemplary embodiment, the monitoring unit 1 displays on the display information that a sign of a fire outbreak has occurred in a monitored section where a pattern of changes in the ratio of the concentration of CO to the concentration of $CO_2$ shows a predetermined pattern.

The gas for which the state is measured to determine whether or not a sign of a fire outbreak has occurred may be other than CO or $CO_2$. Further, based on the state of a single gas, it may be determined whether or not a sign of a fire outbreak has occurred.

Further, other modifications of each of the above exemplary embodiments will be described.

In each of the above exemplary embodiments, the laser transmitter/receiver 3 has a function of transmitting an optical signal and a function of receiving the optical signal reflected by the reflector 4. The device (laser transmitter) having the function of transmitting the optical signal and the device (laser receiver) having the function of receiving the optical signal may be provided separately. In this case, the reflector 4 need not be provided. In this configuration, the laser transmitter includes, for example, laser light sources 301, 311, drivers 302, 312, and condensers 303, 313, as shown in FIG. 7. The laser receiver includes, for example, condensers 321, 331, photodetectors 322, 332, signal processing units 323, 333, a calculation unit 340, and a communication unit 341, as shown in FIG. 7. Each of these elements is the same as each of the elements shown in FIG. 7 and will not be described.

In this modification, the laser transmitter receives an optical signal directed to the laser receiver, and the laser receiver receives the optical signal. A section between the laser transmitter and the laser receiver is the monitored section assigned to the pair of the laser transmitter and the laser receiver. In this modification, the sensor unit 2 assigned to the pair of the laser transmitter and the laser receiver is communicably connected with at least the laser receiver. Furthermore, the laser transmitter may also be communicably connected to the sensor unit 2.

Further, other modifications of each of the above exemplary embodiments will be described.

Figure 19:
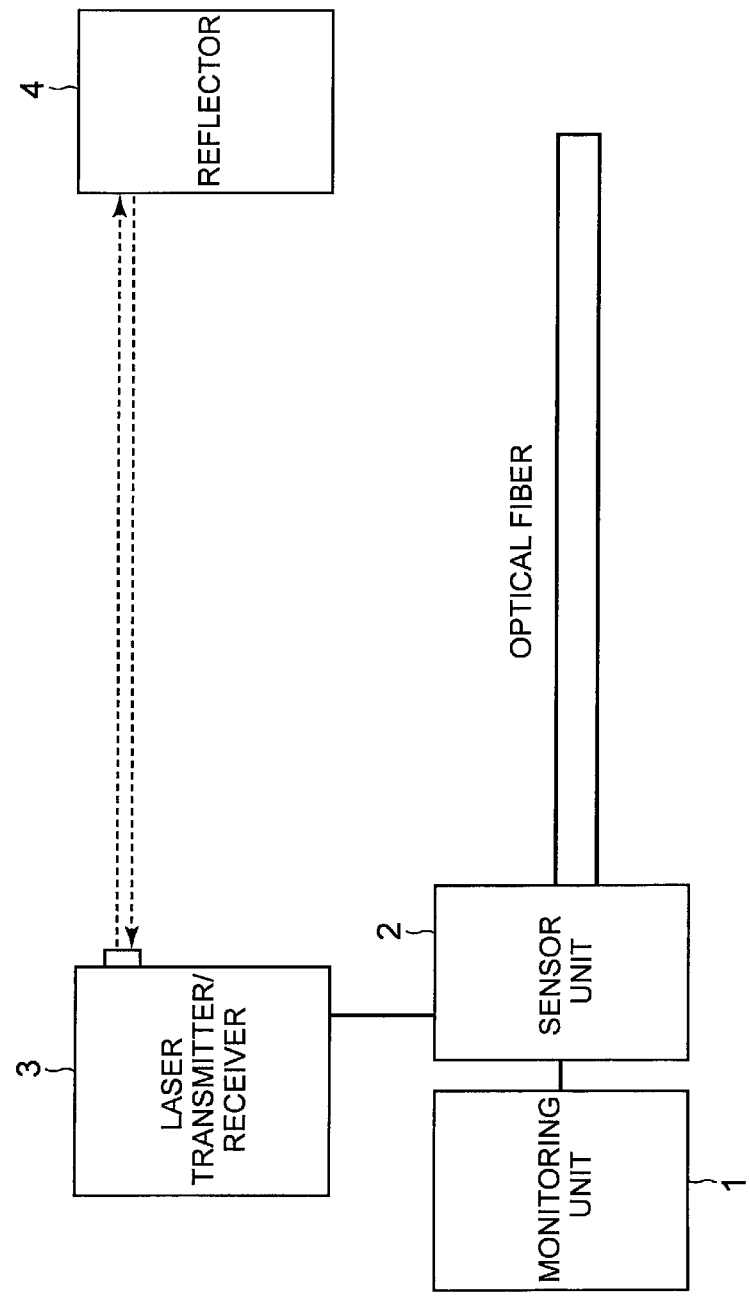
FIG. 19 It depicts a schematic diagram showing an example of a fire detection system having one sensor unit 2 and a pair of a laser transmitter/receives 3 and a reflector 4.

In each of the above exemplary embodiments, a fire detection system comprising a monitoring unit 1, a plurality of sensor units 2, and a plurality of pairs of a laser transmitter/receiver 3 and a reflector 4 is described. The number of sensor units 2 included in the fire detection system may be one. The number of pairs of a laser transmitter/receiver 3 and a reflector 4 included in the fire detection system may be one pair. When the number of sensor units 2 is one, both ends of the optical fiber may be connected to that one sensor unit 2. When the number of sensor units 2 is one, the sensor units 2 need only be connected to the monitoring unit 1, and the third optical fiber 13 in the first exemplary embodiment and the second optical fiber 76 in the second exemplary embodiment may not be provided. Further, as mentioned above, the first optical fiber 11 and the second optical fiber 12 in the first exemplary embodiment may be realized by one optical fiber. In this case, both ends of that one optical fiber may be connected to that one sensor unit 2. FIG. 19 is a schematic diagram showing an example of a fire detection system with one sensor unit 2 and one pair of a laser transmitter/receiver 3 and a reflector 4.

In each of the above exemplary embodiments, the monitoring unit 1 may control each sensor unit 2 and each laser transmitter/receiver 3 in response to an operation of an operator. For example, the monitoring unit 1 may transmit a control signal requesting a log to each sensor unit 2 and each laser transmitter/receiver 3, and each sensor unit 2 and each laser transmitter/receiver 3 may transmit a log to the monitoring unit 1 in accordance with the control signal. However, the operation of the monitoring unit 1 controlling each sensor unit 2 and each laser transmitter/receiver 3 in response to an operation of an operator is not an essential technical matter in the present invention. Therefore, the details of the operation of each sensor unit 2 and each laser transmitter/receiver 3 to generate a log and the like are not described in detail.

The present invention can be used, for example, in road and railroad tunnels. Further, the present invention can also be used in oil and gas plants.

Figure 20:
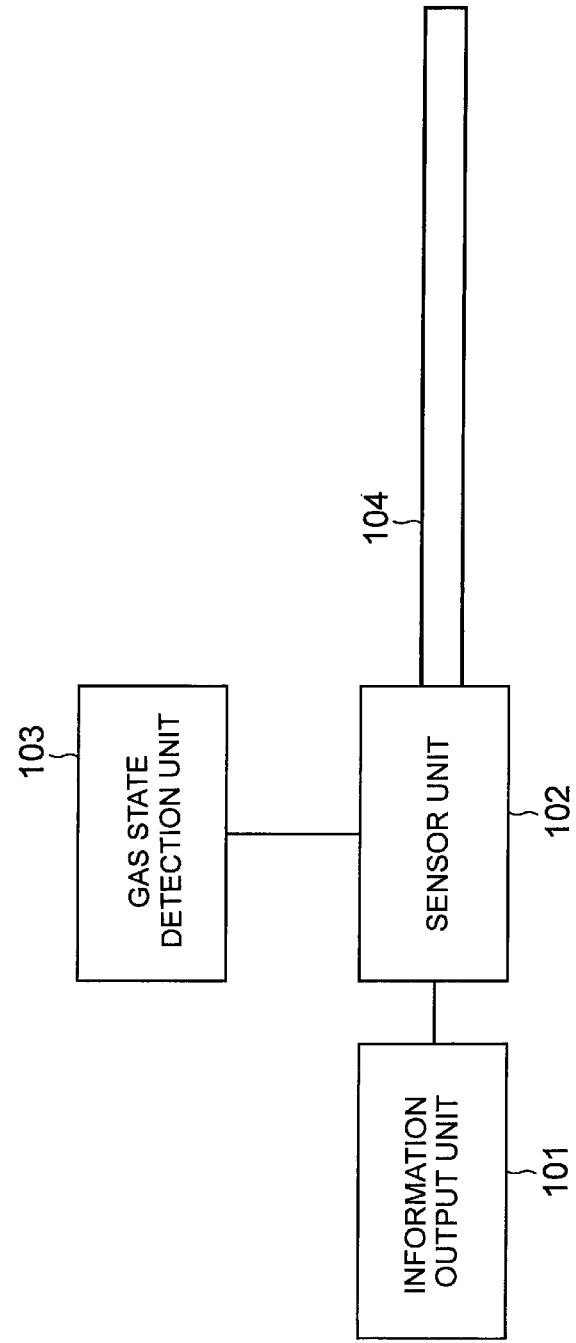
FIG. 20 It depicts a block diagram showing a summarized example of the fire detection system of the present invention.

Next, an overview of the present invention will be described. FIG. 20 is a block diagram showing a summarized example of the fire detection system of the present invention. The fire detection system of the present invention comprises a sensor unit 102 (e.g., the sensor unit 2 in the first exemplary embodiment) installed in an optical fiber 104, a gas state detection unit 103 (e.g., the laser transmitter/receiver 3 in the first exemplary embodiment) that detects a state of gas, and an information output unit 101 (e.g., the monitoring unit 1 in the first exemplary embodiment) that outputs information.

When the sensor unit 102 detects a location which vibration reached in the optical fiber, 104, the sensor unit 102 transmits information indicating the location to the information output unit 101.

The gas state detection unit 103 transmits information indicating the state of gas to the information output unit 101.

The information output unit 101 receives information indicating the location which vibration reached in the optical fiber 104, receives information indicating the state of gas, and outputs information that a sign of a fire outbreak has occurred at the location when the state of gas meets a predetermined condition.

Such a configuration allows to detect locations early where there is a possibility of fire outbreak.

Figure 21:
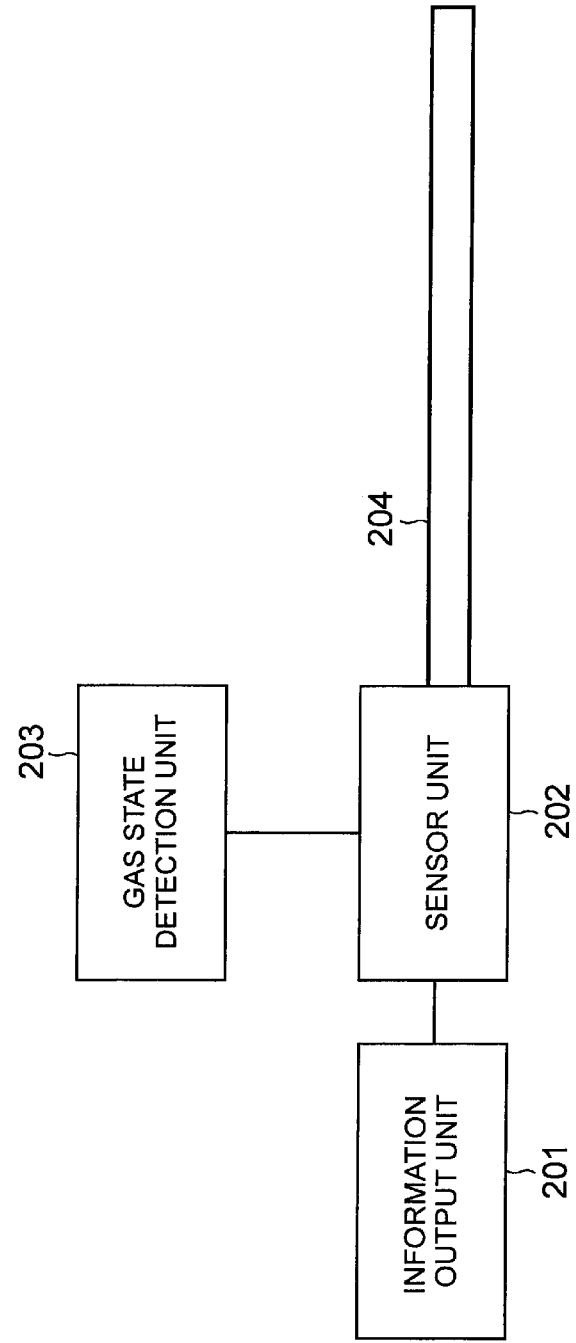
FIG. 21 It depicts a block diagram illustrating another summarized example of the fire detection system of the present invention.

FIG. 21 is a block diagram showing another summarized example of the fire detection system of the present invention. The fire detection system of the present invention comprises a sensor unit 202 (e.g., the sensor unit 2 in the second exemplary embodiment) installed in an optical fiber 204, a gas state detection unit 203 (e.g., the laser transmitter/receiver 3 in the second exemplary embodiment) that detects a state of gas, and an information output unit 201 (e.g., the monitoring unit 1 in the second exemplary embodiment) that outputs information.

The gas state detection unit 203 transmits information indicating the state of gas to the information output unit 201.

When the sensor unit 202 detects a location where a temperature rise has occurred in the optical fiber 204, the sensor unit 202 transmits information indicating the location to the information output unit 201.

The information output unit 201 receives the information indicating the state of gas, and when the state of gas meets a predetermined condition, the information output unit 201 outputs information that a sign of a fire outbreak has occurred, and when receiving the information the location where a temperature rise has occurred in the optical fiber 204, the information output unit 201 outputs information indicating a fire has occurred at the location.

Such a configuration allows for early detection of a section where a fire may beak out prior to detection of a fire outbreak location.

The aforementioned exemplary embodiments can be described as supplementary notes mentioned below, but are not limited to the following supplementary notes.

(Supplementary note 1) A fire detection system comprises:
one or more sensor units installed in an optical fiber,
a gas state detection unit which detects a state of gas, and
an information output unit which outputs information, wherein
when detecting a location which vibration reached in the optical fiber, the sensor unit transmits information indicating the location to the information output unit,
the gas state detection unit transmits information indicating the state of gas to the information output unit, and
the information output unit receives the information indicating the location which the vibration reached in the optical fiber and the information indicating the state of gas, and outputs information indicating a sign of a fire outbreak occurred at the location when the state of gas meets a predetermined condition.

(Supplementary note 2) The fire detection system of Supplementary note 1,
wherein
when detecting a location where a temperature rise occurred in the optical fiber, the sensor unit transmits information indicating the location to the information output unit, and
when receiving the information indicating the location, the information output unit outputs information indicating that a fire has broken out at the location.

(Supplementary note 3) The fire detection system of Supplementary note 1 or 2,
wherein
when receiving the information indicating the location which the vibration reached in the optical fiber, the information output unit outputs information indicating that there is a possibility of occurring an accident at the location.

(Supplementary note 4) The fire detection system of any one of Supplementary notes 1 to 3,
wherein
a plurality of gas state detection units is provided,
each of the gas state detection units transmits information indicating the state of gas and information indicating a monitored section assigned to the gas state detection unit, to the information output unit, and
the information output unit outputs the information indicating the sign of a fire outbreak occurred at the location, when the location which vibration reached in the optical fiber is within the monitored section where the state of gas meets the predetermined condition.

(Supplementary note 5) The fire detection system of any one of Supplementary notes 1 to 4,
wherein
when the state of gas meets the predetermined condition, the gas state detection unit transmits the information to that effect to the information output unit.

(Supplementary note 6) The fire detection system of any one of Supplementary notes 1 to 5,
wherein
a plurality of gas state detection units is provided, each of the gas state detection units detects concentration of a first gas and concentration of a second gas, and when a ratio of the concentration of the first gas to the concentration of the second gas is greater than a threshold, transmits information that the ratio is greater than the threshold and information indicating a monitored section assigned to the gas state detection unit to the information output unit, and
the information output unit receives the information indicating the location which the vibration reached in the optical fiber, receives the information that the ratio is greater than the threshold and the information indicating the monitored section, and outputs the information indicating the sign of a fire outbreak occurred at the location when the location is within the monitored section.

(Supplementary note 7) The fire detection system of any one of Supplementary notes 1 to 4,
wherein
a plurality of gas state detection units is provided,
each of the gas state detection units detects concentration of a first gas and concentration of a second gas, and transmits information indicating the concentration of the first gas, the concentration of the second gas and a monitored section assigned to the gas state detection unit, to the information output unit, and
the information output unit receives the information indicating the location which the vibration reached in the optical fiber, receives the information indicating the concentration of the first gas, the concentration of the second gas and the monitored section assigned to the gas state detection unit, and outputs the information indicating the sign of a fire outbreak occurred at the location, when the location is within the monitored section and a ratio of the concentration of the first gas to the concentration of the second gas is greater than a threshold.

(Supplementary note 8) The fire detection system of any one of Supplementary notes 1 to 5,
wherein
a plurality of gas state detection units is provided, each of the gas state detection units detects concentration of a first gas and concentration of a second gas, and when a pattern of changes in a ratio of the concentration of the first gas to the concentration of the second gas shows a predetermined pattern, transmits to the information output unit information that the pattern of changes in the ratio shows the predetermined pattern, and information indicating a monitored section assigned to the gas state detection unit, and the information output unit receives the information indicating the location which the vibration reached in the optical fiber, receives the information that the pattern of changes in the ratio shows the predetermined pattern and the monitored section, and outputs the information indicating the sign of a fire outbreak occurred at the location, when the location is within the monitored section.

(Supplementary note 9) The fire detection system of any one of Supplementary notes 1 to 4,
wherein
a plurality of gas state detection units is provided,
each of the gas state detection units detects concentration of a first gas and concentration of a second gas, and transmits information indicating the concentration of the first gas, the concentration of the second gas and a monitored section assigned to the gas state detection unit, to the information output unit, and
the information output unit receives the information indicating the location which the vibration reached in the optical fiber, receives the information indicating the concentration of the first gas, the concentration of the second gas and the monitored section assigned to the gas state detection unit, and outputs the information indicating the sign of a fire outbreak occurred at the location, when the location is within the monitored section and a pattern of changes in a ratio of the concentration of the first gas to the concentration of the second gas shows a predetermined pattern.

(Supplementary note 10) A fire detection system comprises:
one or more sensor units installed in an optical fiber,
a gas state detection unit which detects a state of gas, and
an information output unit which outputs information,
wherein
the gas state detection unit transmits information indicating the state of gas to the information output unit,
when detecting a location where a temperature rise has occurred in the optical fiber, the sensor unit transmits information indicating the location to the information output unit, and
the information output unit receives the information indicating the state of gas, outputs information indicating a sign of a fire outbreak occurred when the state of gas meets a predetermined condition, and outputs information indicating a fire has occurred at the location when receiving the information indicating the location.

(Supplementary note 11) The fire detection system of Supplementary note 10,
wherein
a plurality of gas state detection units is provided,
each of the gas state detection units detects concentration of a first gas and concentration of a second gas, and when a ratio of the concentration of the first gas to the concentration of the second gas is greater than a threshold, transmits information that the ratio is greater than the threshold and information indicating a monitored section assigned to the gas state detection unit to the information output unit, and the information output unit outputs information indicating the sign of a fire outbreak occurred in the monitored section, when receiving the information that the ratio is greater than the threshold and the information indicating the monitored section assigned to the gas state detection unit.

(Supplementary note 12) The fire detection system of Supplementary note 10,
wherein
a plurality of gas state detection units is provided,
each of the gas state detection units detects concentration of a first gas and concentration of a second gas, and transmits information indicating the concentration of the first gas, the concentration of the second gas and a monitored section assigned to the gas state detection unit, to the information output unit, and
the information output unit receives the information indicating the concentration of the first gas, the concentration of the second gas and the monitored section assigned to the gas state detection unit, and outputs the information indicating the sign of a fire outbreak occurred in the monitored section, when a ratio of the concentration of the first gas to the concentration of the second gas is greater than a threshold.

(Supplementary note 13) The fire detection system of Supplementary note 10,
wherein
a plurality of gas state detection units is provided,
each of the gas state detection units detects concentration of a first gas and concentration of a second gas, and when a pattern of changes in a ratio of the concentration of the first gas to the concentration of the second gas shows a predetermined pattern, transmits to the information output unit information that the pattern of changes in the ratio shows the predetermined pattern, and information indicating a monitored section assigned to the gas state detection unit, and
the information output unit outputs information indicating the sign of a fire outbreak occurred in the monitored section, when receiving the information that the pattern of changes in the ratio shows the predetermined pattern, and the information indicating the monitored section assigned to the gas state detection unit.

(Supplementary note 14) The fire detection system of Supplementary note 10,
wherein
a plurality of gas state detection units is provided,
each of the gas state detection units detects concentration of a first gas and concentration of a second gas, and transmits information indicating the concentration of the first gas, the concentration of the second gas and a monitored section assigned to the gas state detection unit, to the information output unit, and
the information output unit receives the information indicating the concentration of the first gas, the concentration of the second gas and the monitored section assigned to the gas state detection unit, and outputs the information indicating the sign of a fire outbreak occurred in the monitored section, when a pattern of changes in a ratio of the concentration of the first gas to the concentration of the second gas in the monitored section shows a predetermined pattern.

(Supplementary note 15) An information output device configured to:
receive information indicating a location which vibration reached in an optical fiber from a sensor unit installed in the optical fiber,
receive information indicating a state of gas from a gas state detection unit which detects the state of gas, and
output information indicating a sign of a fire outbreak occurred at the location when the state of gas meets a predetermined condition.

(Supplementary note 16) An information output device configured to:
receive information indicating a state of gas from a gas state detection unit which detects the state of gas,
output information indicating a sign of a fire outbreak occurred when the state of gas meets a predetermined condition, and
when receiving information indicating a location where a temperature rise occurred in an optical fiber from a sensor unit installed in the optical fiber, output information indicating that a fire has broken out at the location.

(Supplementary note 17) A fire detection method applied to a fire detection system comprising a sensor unit installed in an optical fiber, a gas state detection unit for detecting a state of gas, and an information output unit for outputting information, wherein
when a location which vibration reached in the optical fiber is detected, information indicating the location is transmitted to the information output unit, by the sensor unit,
information indicating the state of gas is transmitted to the information output unit, by the gas state detection unit, and
information indicating a sign of a fire outbreak occurred at the location is output by the information output unit, when the information indicating the location which the vibration reached in the optical fiber is received, the information indicating the state of gas is received, and the state of gas meets a predetermined condition.

(Supplementary note 18) A fire detection method applied to a fire detection system comprising a sensor unit installed in an optical fiber, a gas state detection unit for detecting a state of gas, and an information output unit for outputting information, wherein
information indicating the state of gas is transmitted to the information output unit, by the gas state detection unit,
when a location where a temperature rise has occurred in the optical fiber is detected, information indicating the location is transmitted to the information output unit, by the sensor unit,
information indicating a sign of a fire outbreak occurred is output by the information output unit, when the information indicating the state of gas is received and the state of gas meets a predetermined condition, and
information indicating a fire has occurred at the location is output by the information output unit, when the information indicating the location is received.

While the present invention has been described with reference to the exemplary embodiments, the present invention is not limited to the aforementioned exemplary embodiments. Various changes understandable to those skilled in the art within the scope of the present invention can be made to the structures and details of the present invention.

This application claims priority based on Japanese Patent Application No. 2018-137798, filed on Jul. 23, 2018, the disclosures of which are incorporated herein in their entirety.

REFERENCE SIGNS LIST 1 monitoring unit
2 sensor unit
3 laser transmitter/receiver
4 reflector
11 first optical fiber
12 second optical fiber
13 third optical fiber
21 vibration detection sensor
22 temperature detection sensor
23 communication unit

What is claimed is:

1. A fire detection system comprises:
one or more sensors installed in an optical fiber and that when detecting a location at which vibration occurred in the optical fiber, transmit first information indicating the location;
a plurality of gas state detectors that each detect a first concentration of a first gas and a second concentration of a second gas at a corresponding monitored location, and when a pattern of changes in a ratio of the first concentration to the second concentration at the corresponding monitored location matches a predetermined pattern, transmit second information that the pattern of changes matches the predetermined pattern and third information indicating the corresponding monitored location; and
a computer which receives the first, second, and third information and outputs fourth information indicating a sign of a fire outbreak occurred at the location when the location indicated by the received first information is within the corresponding monitored location indicated by the received third information.

2. The fire detection system according to claim 1, wherein
the one or more sensors, when detecting a location where a temperature rise occurred in the optical fiber, the transmit fifth information indicating the location, and
the computer, when receiving the fifth information outputs sixth information indicating that a fire has broken out at the location indicated by the fifth information.

3. The fire detection system according to claim 1, wherein
the computer, when receiving the first information, outputs fifth information indicating that there is a possibility of an accident having occurred at the location indicated by the first information.

4. A fire detection system comprises:
one or more sensors installed in an optical fiber and that when detecting a location at which vibration occurred in the optical fiber, transmit first information indicating the location;
a plurality of gas state detectors that each detect a first concentration of a first gas and a second concentration of a second gas at a corresponding monitored location, and transmits second information indicating the first concentration and the second concentration and third information indicating the corresponding monitored location; and
a computer which receives the first, second, and third information and outputs fourth information indicating a sign of a fire outbreak occurred at the location when the location indicated by the received first information is within the corresponding monitored location indicated by the received third information and when a pattern of changes in a ratio of the first concentration to the second concentration at the corresponding monitored location matches a predetermined pattern.

5. A fire detection method comprising:

transmitting, by one or more sensors installed in an optical fiber, first information indicating a location in the optical fiber when detecting that vibration occurred at the location;

detecting, by each of a plurality of gas state detectors, a first concentration of a first gas and a second concentration of a second gas at a corresponding monitored location, and when a pattern of changes in a ratio of the first concentration to the second concentration at the corresponding monitored location matches a predetermined pattern, transmitting second information that the pattern of changes matches the predetermined pattern and third information indicating the corresponding monitored location; and receiving, by a computer, the first, second, and third information, and outputting fourth information indicating a sign of a fire outbreak occurred at the location when the location indicated by the received first information is within the corresponding monitored location indicated by the received third information.

* * * * *